(12) United States Patent
Marquardt et al.

(10) Patent No.: US 9,958,324 B1
(45) Date of Patent: May 1, 2018

(54) ENCLOSED BENCHTOP RAMAN SPECTROMETRY DEVICE

(71) Applicant: MarqMetrix, Inc., Seattle, WA (US)

(72) Inventors: Brian James Marquardt, Seattle, WA (US); John Scott Van Vuren, Seattle, WA (US); Giora Proskurowski, Seattle, WA (US)

(73) Assignee: MarqMetrix Inc., Seattle, WA (US)

( * ) Notice: Subject to any disclaimer, the term of this patent is extended or adjusted under 35 U.S.C. 154(b) by 0 days. days.

(21) Appl. No.: 15/434,002

(22) Filed: Feb. 15, 2017

(51) Int. Cl.
    G01J 3/00    (2006.01)
    G01J 3/02    (2006.01)
    G01J 1/42    (2006.01)
    G01J 3/44    (2006.01)
    G01J 3/28    (2006.01)

(52) U.S. Cl.
    CPC ............. G01J 3/027 (2013.01); G01J 1/4204 (2013.01); G01J 3/0275 (2013.01); G01J 3/4412 (2013.01); G01J 2003/283 (2013.01)

(58) Field of Classification Search
    CPC ...... G01J 3/32; G01J 3/42; G01J 3/28; G01N 21/31; G01N 21/55
    See application file for complete search history.

(56) References Cited

U.S. PATENT DOCUMENTS

| 5,051,551 | A | 9/1991 | Doyle |
| 5,579,423 | A | 11/1996 | Tanaka et al. |
| 5,688,261 | A | 11/1997 | Amirkhanian et al. |
| 5,693,043 | A | 12/1997 | Kittrell et al. |
| 6,252,661 | B1 | 6/2001 | Hanna |
| 6,416,234 | B1 | 7/2002 | Wach et al. |
| 6,466,323 | B1 | 10/2002 | Anderson et al. |
| 2014/0046166 | A1* | 2/2014 | Tokita .................. A61B 5/0095 600/407 |

OTHER PUBLICATIONS

Allred et al., "Near-Infrared Raman Spectroscopy of Liquids and Solids with a Fiber-Optic Sampler, Diode Laser, and CCD Detector", Applied Spectroscopy 44(7): 1229-1231. Retrieved on Aug. 3, 2017, 3 pages.

(Continued)

*Primary Examiner* — Abdullahi Nur
(74) *Attorney, Agent, or Firm* — Lee & Hayes, PLLC

(57) ABSTRACT

An enclosed benchtop Raman spectrometry device, systems, methods, and techniques related thereto are disclosed. A benchtop Raman spectrometer can comprise an enclosure enclosing a probe and sample. In an embodiment, a compliance component can determine concurrent satisfaction of a group of compliance rules. The compliance rules can relate to contact between the probe and sample, environmental conditions within the enclosure, illumination conditions within the enclosure, an operation state of a viewport allowing direct viewing of a sample-probe interface, etc. While concurrent satisfaction is determined, the release of optical energy for interrogation of the sample via the probe can be enabled. In an embodiment, the probe can comprise a spherical optical element, e.g., a BallProbe®, which can be brought into contact with the sample to perform Raman spectroscopy.

20 Claims, 11 Drawing Sheets

(56) References Cited

OTHER PUBLICATIONS

Angel et al., "Some new uses for filtered fiber-optic Raman probes: In situ drug identification and in situ and remote Raman imaging," (1999), J. Raman Spectrosc. 30:795-805. Retrieved on Aug. 3, 2017, 11 pages.
Aust et al., "In situ analysis of a high-temperature cure reaction in real time using modulated fiber-optic FT-Raman Spectroscopy", (1999) Applied Spectroscopy 53(6): 682-686. Retrieved on Aug. 3, 2017, 5 pages.
Cooney et al., "Comparative study of some fiber-optic remote Raman probe designs. Part I: Model for liquids and transparent solids," (1996) Applied Spectroscopy 50 (7): 836-848. Retrieved on Aug. 3, 2017, 13 pages.
Cooney et al., "Comparative study of some fiber-optic remote Raman probe designs. Part II: Tests of single-fiber, lensed, and flatand bevel-tip multi-fiber probes," (1996) Applied Spectroscopy 50 (7): 849-860. Retrieved on Aug. 3, 2017, 12 pages.
Cooney et al., "Rare-earth-doped glass fiber for background rejection in remote fiber-optic Raman probes: theory and analysis of holmium-bearing glass," (1993) Applied Spectroscopy 47(10): 1683-1692. Retrieved on Aug. 3, 2017, 10 pages.
Dai et al., "Accurate procedure for determining the calibration curve of high-temperature molten salt systems via Raman spectroscopy," (1993) Applied Spectroscopy 47(8): 1286-1288. Retrieved on Aug. 3, 2017, 3 pages.
Dai et al., "Temperature measurement by observation of the Raman spectrum of diamond," (1992) Applied Spectroscopy 44: 1229-1231. Retrieved on Aug. 3, 2017, 3 pages.
Gilmore et al., Quantitative detection of environmentally important dyes using diode laser/fiber-optic Raman Spectroscopy, (1995) Applied Spectroscopy 49(4): 508-511. Retrieved on Aug. 3, 2017, 5 pages.
Lin et al., "Feasibility of quantitative UV resonance Raman spectroscopy with a KrF excimer laser," (1987) Applied Spectroscopy 41:422-427. Retrieved on Aug. 3, 2017, 6 pages.
Ma et al., "Fiber Raman background study and its application in setting up optical fiber Raman probes," (1996) Applied Optics 35(15) 2527-2533. Retrieved on Aug. 3, 2017, 7 pages.
Marquardt et al., "Demonstration of a high precision optical probe for effective sampling of solids by Raman spectroscopy," (Oct. 2001) Proc. SPIE vol. 4469, p. 62-69, Raman Spectroscopy and Light Scattering Technologies in Materials Science, David L. Andrews; Ed. Retrieved on Aug. 3, 2017, 8 pages.
McCreery, et al, "Fiber optic probe for remote Raman spectrometry," (1983) Anal. Chem. 55:146-148. Retrieved on Mar. 3, 2017, 3 pages.
Schwab et al., "Remote, long-pathlength cell for high-sensitivity Raman spectroscopy," (1987) Applied Spectroscopy 11:126-130. Retrieved on Aug. 3, 2017, 5 pages.
Schwab et al., "Normal and resonance Raman spectroelectrochemistry with fiber optic light collection," (1986) Anal. Chem. 58:2486-2492. Retrieved on Aug. 3, 2017, 7 pages.
Trott et al., "Angular resolved Raman scattering using fiber optic probes," (Nov. 1980) Rev. Sci. Instrum. 51 (11): 1493-1496. Retrieved on Aug. 3, 2017, 5 pages.
Wang et al., "In situ monitoring of emulsion polyumerization using fiber-optic Raman spectroscopy," (1982) Applied Spectroscopy 46(11): 1729-1731. Retrieved on Aug. 3, 2017, 3 pages.
Xiao et al., "Quantitative Raman spectral measurements using a diamond-coated all-silica fiber-optic probe," (1998) Applied Spectroscopy 52:626-628. Retrieved on Aug. 3, 2017, 3 pages.
Zheng et al., "Self-referencing Raman probes for quantitative analysis," (Apr. 2001) Applied Spectroscopyo 55(4): 382-388. Retrieved on Aug. 3, 2017, 7 pages.

* cited by examiner

ENCLOSED BENCHTOP RAMAN SPECTROMETRY DEVICE

TECHNICAL FIELD

The disclosed subject matter relates to enclosed benchtop analytical equipment, e.g., benchtop chemical analysis equipment having an enclosure. In some embodiments, the disclosed subject matter relates to optical analysis equipment, e.g., a Ramen spectrometry device.

BACKGROUND

By way of brief background, conventional benchtop analytical equipment, e.g., benchtop Raman spectrometry equipment, etc., is generally configured to provide detailed analytical information about an interrogated sample. In some conventional systems, the Raman spectrometer-to-sample interface, hereinafter the interface, can be exposed, e.g., the interface can lack a housing or other enclosure. In these conventional systems, special considerations generally are made to accommodate safe and effective use of the Raman instrument, e.g., these conventional instruments can be placed on benchtops in special rooms to reduce ambient light, can be placed in fume hoods to remove noxious vapors and fumes emanating from the sample, can require operators to use laser-safe eye protection, etc. In some conventional systems, primitive enclosures can be observed, for example, a lid or box that blocks light transmission to protect eyes and block ambient light but that also typically introduce challenges, such as, positioning a sample for analysis in a convenient manner, difficulty in automating sequential sampling, a lack of environmental control, etc. Improving the integration of Raman technology into usable enclosed benchtop instruments provides advantages over the current state of the art.

DETAILED DESCRIPTION

Figure 1:
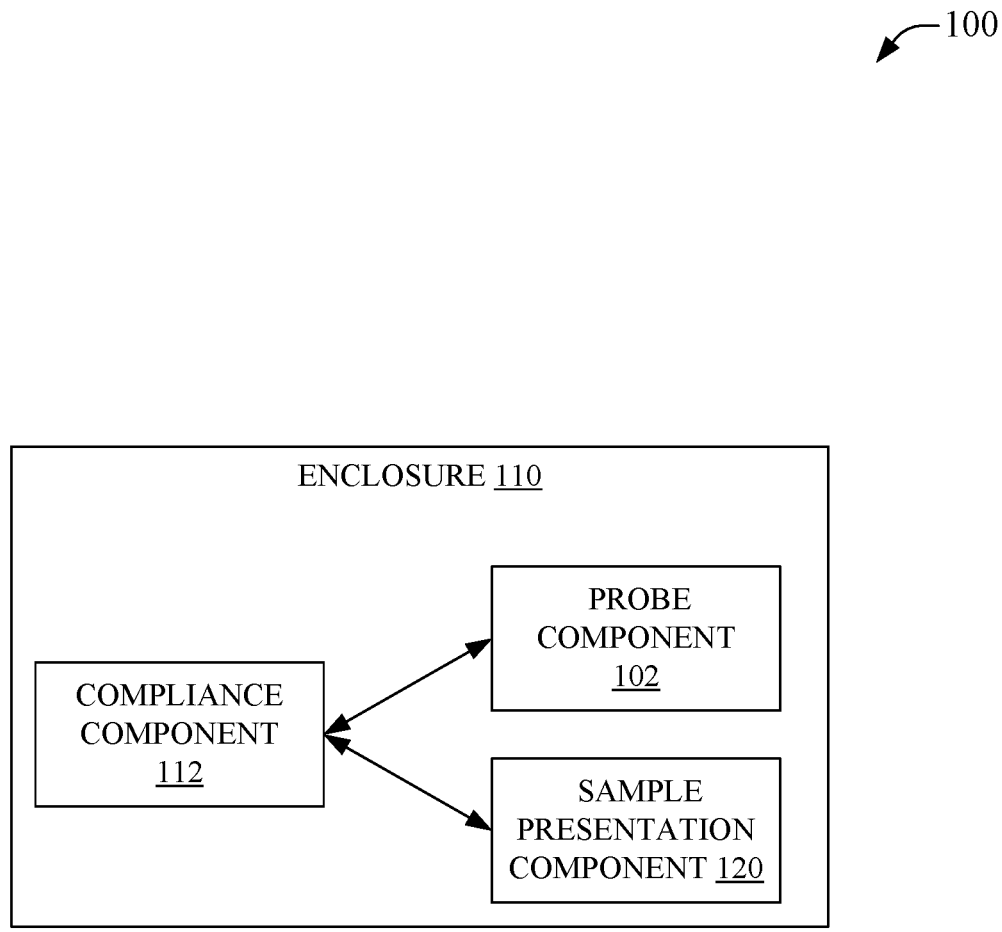
FIG. 1 is an illustration of an example system facilitating enclosing a sample to probe interface in accordance with aspects of the subject disclosure.

The subject disclosure is now described with reference to the drawings, wherein like reference numerals are used to refer to like elements throughout. In the following description, for purposes of explanation, numerous specific details are set forth in order to provide a thorough understanding of the subject disclosure. It may be evident, however, that the subject disclosure may be practiced without these specific details. In other instances, well-known structures and devices are shown in block diagram form in order to facilitate describing the subject disclosure.

Conventional Raman spectrometers were often large industrial sized instruments. Developments in the fields of imaging, e.g., digital cameras, etc., and laser technologies, e.g., for CD-ROMs, etc., have allowed Raman spectrometers to dramatically shrink in size, e.g., to benchtop and even hand-held portable analytical equipment that can provide highly detailed analytical information to a user in the field.

Raman spectrometry typically experiences a great deal of loss in optical power between the interrogating optical energy and the returned optical energy. As such, optical energy sources, e.g., lasers, etc., are often quite powerful to allow for use of affordable detectors. While specialty detectors could allow for use of lower energy interrogation lasers, the cost of the detectors and special operating conditions causes this option to be less viable in a commercial setting. It will be appreciated that powerful lasers can be a danger to human tissue, particularly the human eye. As such, some consideration to shielding an operator is typically associated with all Raman instruments. In some conventional systems, laser-safe eyewear is suggested, in other conventional systems, a rudimentary enclosure can be used to shield the interface between the sample and the Raman instrument. However, these conventional enclosures typically are quite limiting in use. As an example, a sample can be placed in a conventional enclosure, the enclosure can be shut, and the analysis can be performed. However, once the enclosure is closed, there is typically no way of confirming the location of the sample has not changed, there is generally no way of sampling noxious samples short of placing the entire Raman device with the rudimentary enclosure into a fume hood, there is generally no way of regulating the environment of the sample without subjecting the entire Raman device to similar conditions by regulating the environment of the room in which the Raman device is located, etc.

As such, it will be appreciated that an enclosed Raman device addressing the issues of conventionally enclosed Raman instruments can be desirable and can improve the efficiency of Raman spectral analysis, lower training costs, improve safety, allow for analysis of a wider range of samples, etc. To this end, the subject disclosure relates to embodiments of an enclosed benchtop Raman spectrometry device. It will be noted that the disclosed embodiments can be presented separately for clarity and brevity but that combinations of the disclosed embodiments are also considered to be within the scope of the present disclosure, for example, a first embodiment can disclose an enclosure with a viewport and a second embodiment can disclose an enclosure with an environmental control unit, and a third embodiment can disclose an enclosure with an imaging system, accordingly, an embodiment with both a viewport and an environmental control is considered, an embodiment with both a viewport and an imaging system is considered, an embodiment with an imaging system and an environmental control is considered, and an embodiment with a viewport, an environmental control, and an imaging system is considered, etc.

In some embodiments, the disclosed portable analytical equipment can employ a probe component coupled to a controller component. The probe component can be fixed to the controller component, flexibly attached to the controller component, removable attached to the controller component, retractably attached to the controller component, etc. As an example, the probe component can comprise a Ball-Probe® (MarqMetrix Inc., Seattle, Wash.) for Raman immersion testing, contact Raman testing, etc. The probe component can comprise other technologies, e.g., an infrared (IR) probe, an resistance probe, a conductivity probe, a pH probe, a biomarker probe, etc., without departing form the scope of the presently disclosed subject matter as will be appreciated by one of skill in the relevant arts. Moreover, while this disclosure is generally presented in terms of Raman spectroscopy for clarity and brevity, it is asserted that similar advantages can be provided for other benchtop instruments, including those using other optical analysis techniques such as ultraviolet/visible (UV-Vis), near infrared (NIR), mid-infrared (FTIR), fluorescence, etc., and that all such other uses are within the scope of the present disclosure despite not being explicitly recited. Furthermore, in some embodiments, the disclosed subject matter can perform Raman spectroscopy serially or in parallel with other optical analysis techniques such as UV-Vis, NIR, FTIR, fluorescence, etc., e.g., a Raman spectrum can be captured along with another optical analysis for the same sample at substantially the same time, such that an operator does not need to move the sample from a Raman instrument to a NIR instrument, to a FTIR instrument, etc. In some embodiments, the disclosed subject matter can support Raman performed in series or in parallel for multiple excitation energies, e.g., 532 nm, 785 nm, 1064 nm, etc. Further still, some embodiments can combine imaging with Raman spectra, e.g., a picture of the sample and a Raman spectrum for mapped to the picture.

In an embodiment, a system can comprise a compliance component that can interact with other components of the system to ensure that rules are being satisfied before enabling an analysis to proceed. In an aspect, this can allow designation of procedures, tolerances, and safety measures to be automatically monitored before allowing the analysis to proceed. As an example, a contact sensor can verify that an enclosure is closed before allowing a release of laser light to interrogate a sample, which can prevent the laser emission while the enclosure is not closed to protect an operator. As another example, a light sensor can be monitored to ensure the sample is in darkness before the analysis can proceed, which can reduce artifacts in the spectral results that can occur when ambient light is present. As a further example, a temperature within the enclosure can be monitored to allow a sample to be at a known state before the analysis is enabled to proceed, which can reduce variation between analytical runs that can result from operators opening and closing an enclosure between runs. A compliance component can receive input from various sensors, monitors, user inputs, etc., to coordinate a release of a hold on an analysis, e.g., the analysis can occur in response to the concurrent satisfaction of one or more compliance rules. As an example, an operator can place a sample in an enclosure having an imaging system and a sample contact sensor. The example operator can then position a Raman probe at an area of interest on the sample. The imaging system can then be switched to a non-illumination mode to reduce light pollution and the example Raman probe can be advanced against the sample. In this example, the compliance component can determine that the enclosure is properly closed, that concurrently the illumination source is off, and can wait for the contact sensor to concurrently indicate that the Raman probe has contacted the sample. Upon the sample being contacted by the Raman probe, the contact sensor can indicate that contact has been made, which can satisfy a contact rule concurrently with the lights being off and the enclosure being closed, and can result in the analysis being allowed to proceed, e.g., the concurrent satisfaction of the conditions can start the analysis. This can allow an operator to simply place the sample, close the door, position the sample via a camera, and move the probe to contact the sample, whereupon the analysis is triggered and the operator can begin the subsequent analysis. Moreover, expanding the prior example, an array of samples, e.g., placed on a 96-well plate, etc., can be placed in an embodiment of the disclosed subject matter, the enclosure can be closed, the operator can move, with the help of an internal video camera and illuminator, the probe to the first of the 96 wells in the plate and press a start button. In response, the example system can shut off the illuminator and begin a stage translation process to bring the probe into contact with each well of the 96-well plate sequentially. The example compliance controller can verify that the enclosure is closed, that the illuminator is off, and can enable the Raman interrogation laser only when the probe is determined to be in contact with the sample plate, e.g., at each well as the translation process cycles the probe contact with each well, concurrent with the illuminator being off and the enclosure being closed. As such, should the enclosure be opened, the compliance component can prevent the release of laser energy.

In an embodiment, a system can comprise an imaging component within the enclosure. This can enable remote observation of the interior of the enclosure. As illustrated in previous examples, the imager/illuminator can enable an operator to position a probe relative to a sample without needing to open the enclosure. In contrast to typical conventional benchtop Raman instruments, this can enable an operator to interrogate different portions of a sample by placing the sample in the enclosure, closing the enclosure, and then interacting with the sample interface via imaging and remote control of the sample stage and/or Raman probe tip. As an example, where an inhomogeneous ore sample is placed in the enclosure, an analysis at a first location on the ore can provide a first result. The operator can then reposition the sample/probe to a second location via the imager to capture a second result. While this can appear trivial, there can be significant timesaving in enabling remote repositioning of the sample/probe rather than opening the enclosure to reposition a sample directly. Moreover, imaging and illumination can be done in spectral regions beyond human eyesight, e.g., IR, NIR, UV, etc., which can allow an operator to position a sample/probe relative to features that might not be visible to the human eye directly. As an example, a coral sample can comprise biological materials that fluoresce in UV light, allowing an operator to position the probe/sample via a UV sensitive imager and UV illuminator, then shifting off the UV illuminator to allow for Raman analysis of at the selected location on the coral.

In some embodiments, a viewport can be included through the enclosure. In an aspect, this viewport can be optically transparent at select wavelengths to allow direct viewing of an analysis with operator safety and reduction of artifacts in the captured spectrum. As an example, the viewport can comprise a laser safe window to attenuate laser light that can escape the sample interface, which can protect an operator. As another example, the view port can comprise a shutter, sliding plate, etc., that can physically block light transmission. In this example, the operator can directly view the sample, for example to position it, then can provide an input, e.g., press a start button, etc., that can trigger a shutter to close, the analysis to proceed, and then the shutter to open. The shuttering process can be kept brief, being perhaps just slightly longer than the time needed to interrogate the sample optically. In an aspect, the shutter can 'blink' to protect the operator from laser light and to shield the interface from ambient light. Whereas the compliance component can enable the release of the laser energy when the shutter is closed, the action of triggering the shutter can in effect also cause the laser to fire on the sample. It will be noted that heuristic timing can be easily incorporated into the example to provide for a slight delay after the triggering of the shutter before lasing the sample begins, and correspondingly, a slight delay between the end of lasing and the reopening of the shutter.

In an embodiment, the disclosed subject matter can comprise an environmental control component. The environmental control component can enable control of the environment within an enclosure. This can facilitate analysis of delicate samples, hazardous samples, etc. As an example, the environmental control component can keep the sample area at a temperature, e.g., below freezing to allow analysis of icy samples, at standard temperature and pressure (STP) to allow analysis to be performed independent of temperature or pressure variation, etc. As another example, the environmental control component can vent the enclosure to a fume hood, scrubber, etc., to enable analysis of volatile compounds. As a further example, the environmental control component can control humidity, for example to ramp humidity to illustrate a rate of absorption of water into a sample over time by monitoring the change in water in a sample as absorbed from the humidified air over time. In a still further example, the environmental control component can maintain a gaseous environment, for example, an inert environment by filling the enclosure with helium, dry nitrogen, etc., a reactive environment by allowing a fixed amount of oxygen into the enclosure for an analysis of an oxidative event, etc.

In some embodiments, the disclosed subject matter contemplates that the position of the optical interrogation of a sample can be altered. In an aspect, this can be achieved by moving the probe relative to the sample, moving the sample relative to the probe, or both moving the sample and the probe relative to each other. In this disclosure, except where explicitly disclosed as being exclusive of other relative movement, descriptions of moving the sample can be accomplished by these or other techniques, e.g., changing the focal position of the interrogating optical energy with or without movement of the probe or the sample, etc. In effect, the present disclosure is, in part, directed to analysis of different portions of a sample within the enclosed area of the disclosed device or system. As an example, where a sample is liquid and the probe is dipped in to the liquid, e.g., in-situ analysis, different portions of the sample can be analyzed at least by moving the probe tip in the sample, moving the sample around the probe, moving bother the probe and the sample, changing a focal length of the interrogating laser to sample a different aura of the sample with/without moving the sample and/or probe, flowing the sample past the probe, etc.

Moreover, in some embodiments, the probe tip can be consumable or exchangeable. This can be in lieu of, or in addition to, the probe tip being cleanable. It will be appreciated that repeated use of a probe time without cleaning can result in changes to the condition of the probe tip that can alter captured results. As an example, contact of a probe tip with tar can result in the tar adhering to an optical element of the probe and preventing accurate results in following analytical runs of the instrument. In these situations, the tip can be cleaned or exchanged. In an aspect, this can occur in the enclosure. Moreover, some samples can be affiliated with particular types of tips, for example, sampling of concentrated hydrofluoric acid can be better performed with a plastic lens probe tip than a glass lens probe tip. As another example, a first depth of focus can be desired for a first analysis and a different second depth of focus can be desired for another analysis. The disclosed subject matter can comprise a cleaning component to enable cleaning of a probe tip. Moreover, the disclosed subject matter can comprise a battery of other probe tips to allow for replacement of consumed probe tips, exchange of tips suited to an analysis, etc. As an example, a probe tip dipped in tar can be moved to the cleaning component and a different probe tip can be substituted. This can allow the analysis to continue while the first tip is being cleaned. In another example, a damaged tip can be disposed of and a replacement tip can be retrieved from the battery of tips. In a further example, a first tip can be used for a first analysis and then a second tip can be used for a second analysis without needing to open the enclosure. Moreover, the compliance component can, in some embodiments, check the condition of a probe tip to determine if replacement of the tip should occur, e.g., a self-diagnostic, calibration, etc.

Overall, a benchtop Raman spectrometer with an enclosure according to one or more of the disclosed embodiments can serve to improve the operation and implementation of Raman spectrometers by allowing for safer operation, improved automation, a wider degree of allowed samples, self-diagnosis of consumable elements, etc. Some disclosed embodiments allow the operator to directly view the sample/ probe interface for positioning into areas of interest, can extend the human senses by incorporating imaging devices, can allow work with fragile or dangerous samples, in an automated manner with a variety of instrumental modes, while monitoring a condition of the instrument and providing a safer and more comfortable bench top analysis environment.

To the accomplishment of the foregoing and related ends, the disclosed subject matter, then, comprises one or more of the features hereinafter more fully described. The following description and the annexed drawings set forth in detail certain illustrative aspects of the subject matter. However, these aspects are indicative of but a few of the various ways in which the principles of the subject matter can be employed. Other aspects, advantages and novel features of the disclosed subject matter will become apparent from the following detailed description when considered in conjunction with the provided drawings.

FIG. 1 is an illustration of a system 100, which facilitates enclosing a sample to probe interface in accordance with aspects of the subject disclosure. System 100 can comprise enclosure 110. Enclosure 110 can enclose an interface between a sample and an analytical instrument. In an embodiment, enclosure 110 can enclose probe component 102 and sample presentation component 120. Probe component 102 and sample presentation component 120 can be communicatively coupled to compliance component 112. In some embodiments, enclosure 110 can be a configured to rest on a surface, such as a table, bench, etc., and support probe component 102 and sample presentation component 120, to allow an operator to open a portion of enclosure 110 to place a sample on sample presentation component 120 such that probe component 102 can enable analysis of the sample within enclosure 110, e.g., enclosure 110 can appear to be an enclosed benchtop Raman spectrometer, etc.

In an embodiment, probe component 102 can comprise an interface for an analytical instrument to interrogate a sample, e.g., in a Raman spectrometer instrument, probe component 102 can direct optical energy at a sample. In an embodiment, probe component 102 can comprise an optical element, e.g., a lens, etc. that directs optical energy at a sample. In an example, probe component 102 can comprise a spherical optical element. The spherical optical element can be a BallProbe® (MarqMetrix Inc., Seattle, Wash.). A BallProbe® can enable Raman spectrometry. In an aspect, a BallProbe® can allow for in-situ Raman spectrometry via probe component 102. An example benchtop analytical device comprising a BallProbe® can perform Raman spectrometry by dipping or inserting the BallProbe® into a sample, against a sample, etc., and initiating an analytical interrogation of said sample. The analytical interrogation can excite atomic bonds of molecules in the sample such that a Raman spectrum can be captured, e.g., a response form sample interrogation. The Raman spectrum can then be analyzed. The analysis of the Raman spectrum can be based on reference Raman spectra. Of note, the terms 'spectrometry' and 'spectroscopy' are frequently used interchangeably in the art, though they can have slightly different connotations. The term 'spectrometry' is used in this disclosure in relation to the capture, analysis, and generation of results based on spectral information elicited via interrogation of a sample, as 'spectrometry' is believed to be the more correct term in this regard. However, the term 'spectrometry' is to be treated as inclusive of the common connotation of the term 'spectroscopy' as used by those of skill in the related art, unless otherwise explicitly indicated as having a narrower or different meaning in this disclosure.

In an aspect, embodiments of probe component 102 can be constructed of nearly any material suitable to an expected sample environment. Probe component 102 can comprise a suitable polymer, e.g., polypropylene (PP), polyethylene terephthalate (PET), silicone, polytetrafluoroethylene (PTFE), etc. Probe component 102 can comprise other materials, such as, but not limited to, stainless steel, gold, or other metal; borosilicate or other glass; starches or other carbohydrates, etc.; or nearly any other material suitable to a particular sample environment. Moreover, materials can be machined, sintered, cast, injection molded, 3D-printed, etc., for example to form a body, optical element seat, shroud, etc., of probe component 102. Moreover, in some embodiments, an optical element can be 'spherical,' and can be separately manufactured and added to the body, either as part of a molding process, bonded with an adhesive, attached with a friction or press fit, mechanically captured, etc. In other embodiments, the 'spherical' optical element can be co-formed with the body as part of a molding process, e.g., the spherical optical element can be formed, of the same or a different material, with the removable optical assembly in injection molding; can be formed, of the same or a different material, with the removable optical assembly in 3D printing; etc. Additionally, 'spherical' optics can be manufactured from nearly any appropriate material, including the same or different materials as the body of a removable optical assembly. Non-limiting examples of appropriate materials can include a polymer, glass, mineral, etc., depending on the optical properties suited to a given scenario. Of note, the term 'spherical' optical element, or similar terms, as used herein, generally means an optical element, e.g., a lens, etc., that has a spherical, or nearly spherical, geometry. Moreover, the term 'spherical optical element,' as used herein, also includes any optical element that conducts light via a portion of the optical element that comprises a curved surface approximating at least a portion of a sphere, for example, where sphere of optical glass has an shallow equatorial trench ground into it, such as to capture a retaining ring, etc., the resulting optical element, within the context of the instant disclosure, would still be considered a spherical optical element so long as light enters/exits the non-equatorial portions. As another example, an injection molded spherical optical element can comprise a protrusion, e.g., resembling a lollipop on a stick, and, within the context of the instant disclosure, would still be considered a spherical optical element. As a further example, an optical element comprising two individual hemispherical portions can also be considered a spherical element within the scope of the instant disclosure.

Sample presentation component 120 can comprise a sample retention portion that can retain a sample. In an aspect, sample presentation component 120 can comprise a motion component allowing controlled motion of a sample stage. In a further aspect, sample presentation component 120 can comprise a sensing component allowing for detection of interaction with a sample supported by a sample stage. In another aspect, sample presentation component 120 can comprise a sample-arranging portion that allows placement of a sample for retention. As examples, sample presentation component 120 can be a liquid flow cell, a gas flow cell, a sample stage, etc. As other examples, sample presentation component 120 can be a sample stage with a multi-well plate connector allowing a multi-well plate to be connected to the sample stage. This example sample stage, in some embodiments can be connected to a translation component that can move the sample stage, and thereby the multi-well plate relative to probe component 102. This can enable sequential analysis of samples in one or more wells of the multi-well plate. In an aspect, a flow cell for either gas or liquid can be manifolded to enable handling of multiple gas/liquid streams, e.g., multiple sample inputs, reagent inputs, cleaning agent inputs, etc.

Enclosure 110 can provide optical separation from the interface between the sample and a probe. This can reduce the risk of an operator being exposed to optical energy that can escape from the interface area. Moreover, the enclosure can reduce ambient light entering the interface, which can thereby reduce errors in analysis resulting from stray light reaching an optical detector of the benchtop instrument.

Compliance component 112 can be communicatively coupled to one or more of the enclosure 110, probe component 102, and sample presentation component 120. Compliance component 112 can receive a compliance rule related to an aspect of system 100. Compliance component 112 can determine that the compliance rule has been satisfied. In an aspect, compliance component 112 can determine concurrent compliance with a group of compliance rules related to aspects of system 100. As an example, compliance component 112 can determine that an aspect of probe component 102, and aspect of sample presentation component 120, and an aspect of enclosure 110 are concurrently compliant. As a more detailed example, probe component 102 can be determined to be compliant based on determining than an attached probe is fit for a designated analysis profile, sample presentation component 120 can be determined to be compliant based on detecting that contact has been made with a sample on the sample presentation component 120, and enclosure 110 can be determined to be compliant based on output from a sensor associated with detecting when the enclosure is closed, such that the compliance component can determine that, concurrently, the correct probe is on, the enclosure is closed, and the probe has been put into contact with the sample of the sample presentation component 120.

In an embodiment, compliance component 112 can enable access to data relating to determining compliance with one or more compliance rules, e.g., an operator can access information showing that the enclosure is not showing as 'closed,' a system comprising a processor can receive information indicating which probe is determined to be attached to probe component 102, etc.

In another aspect, compliance component 112 can enable interrogation of the sample to proceed, e.g., release of optical energy to the sample can be in response to compliance component 112 determining that the group of compliance rules is concurrently satisfied. This aspect can reduce opportunities for release of laser energy, for example, where the enclosure is not properly closed, where the wrong probe is on probe component 102, where the probe is not in proper position/contact with the sample, etc. Moreover, this aspect can act as a trigger, such that as the compliance rules of the group of compliance rules progress towards contemporaneous compliance, the Raman spectrometer stands ready to interrogate the sample but cannot until the instant compliance component 112 determines that there is contemporaneous satisfaction of the compliance rules. In a further aspect, where one or more of the rules goes into non-compliance, compliance component 112 can determine that concurrent compliance is not occurring and can stop enabling release of optical energy, e.g., compliance component 112 can suspend or terminate the interrogation of a sample where any condition of system 100 represented by a compliance rule of the group of compliance rules transitions from satisfied to not satisfied. As an example, the emission of optical energy can be stopped where the enclosure is opened, where the probe is not in contact with the sample, etc.

Figure 2:
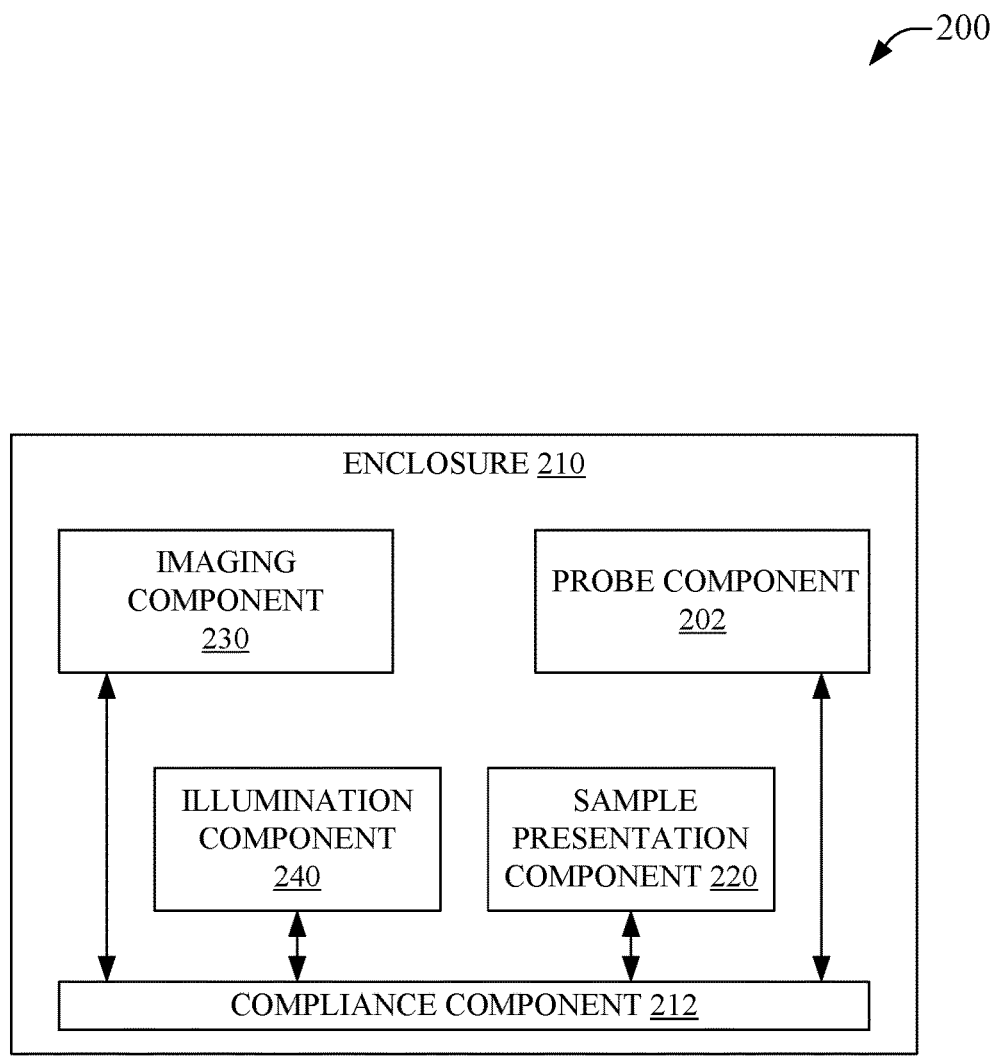
FIG. 2 is a depiction of an example system that facilitates indirect monitoring of a sample to probe interface for an optical analytical instrument comprising an enclosure in accordance with aspects of the subject disclosure.

FIG. 2 is a depiction of a system 200 that can facilitate indirect monitoring of a sample to probe interface for an optical analytical instrument comprising an enclosure in accordance with aspects of the subject disclosure. System 200 can comprise enclosure 210. Enclosure 210 can enclose an interface between a sample and an analytical instrument. In an embodiment, enclosure 210 can enclose probe component 202 and sample presentation component 220. Probe component 202 and sample presentation component 220 can be communicatively coupled to compliance component 212.

In an embodiment, probe component 202 can comprise an optical element to direct optical energy at a sample. In an embodiment, the optical element that directs optical energy at a sample can comprise a spherical optical element. A spherical optical element can be a BallProbe® that can enable Raman spectrometry via probe component 202. An example benchtop analytical device comprising probe component 202 can perform Raman spectrometry by dipping or inserting a portion of probe component 202 into a sample, against a sample, etc., and initiating an optical interrogation of said sample.

In an embodiment, sample presentation component 120 can present a sample for interrogation via probe component 202. In an aspect, sample presentation component 120 can move relative to probe component 202, e.g., in the x-axis, y-axis, z-axis, rotationally, etc., so as to be able to present different portions of a sample, different samples, etc., for analysis via probe component 202. A position of sample presentation component 220 and probe component 202 can be determined, e.g., via compliance component 212, via sample presentation component 22, via a connected controller/computer, etc. The position can be employed to determine that the sample is appropriately oriented for optical interrogation. In an aspect, where a BallProbe® is employed, contact Raman spectroscopy can be performed, e.g., the spherical optical element can be placed directly against the sample, or in the sample, to interrogate the sample. In contact Raman, a position between probe component 202 and the sample can be determined based on pressured applied between the probe component 202 and the sample, e.g., as measured at the sample presentation component 220, etc., such that the BallProbe® can be brought into contact with the sample to perform the analysis, preferably without damage to the BallProbe® from the contact. In some embodiments, sample presentation component 220 can comprise a liquid flow cell, a gas flow cell, a sample stage, etc. In some example embodiments, sample presentation component 220 can comprise a multi-well plate, e.g., a 384-, 96-, 48-, 24-, 12-, 6-well plate sample container, etc. This can enable analysis of samples in one or more wells of the multi-well plate.

Enclosure 210 can provide optical separation about the interface between a sample and a probe of the probe component 202. This can improve operator safety by blocking or attenuating optical emissions, e.g., scattered or reflected laser light, etc. Moreover, the enclosure can reduce ambient light entering the interface that can cause errors in the Raman analysis. In some embodiments, enclosure 210 can comprise optical attenuation features, e.g., paint and materials that absorb ambient light to reduce the effect of stray light reaching the detector during capture of a Raman spectrum.

Enclosure 210 can further enclose imaging component 230 and illumination component 240. Imaging component 230 and illumination component 240 can enable remote viewing of the interior of enclosure 210, more particularly a sample and the orientation of the sample and probe component 202 as facilitated by positioning of the sample presentation component 220 and probe component 202. In an aspect, imaging component 230 and illumination component 240 can illuminate and image the presentation of the sample to probe component 202 in the human visible spectrum. In some embodiments, imaging component 230 and illumination component 240 can also illuminate and image the presentation of the sample to probe component 202 in spectrum outside of the normal range of human vision, e.g., UV, IR, etc. Moreover, imaging component 230 and illumination component 240 can be communicatively coupled to compliance component 212. This can enable compliance component 212 to determine the state of imaging component 230 and illumination component 240 with regard to compliance rules for system 200.

Compliance component 212 can be communicatively coupled to one or more of the enclosure 210, probe component 202, sample presentation component 220, imaging component 230, illumination component 240, etc. Compliance component 212 can receive a compliance rule related to an aspect of system 200. Compliance component 212 can determine that the compliance rule has been satisfied. In an aspect, compliance component 212 can determine concurrent compliance with a group of compliance rules related to aspects of system 200. As an example, compliance component 212 can determine that the position of probe component 202 relative to sample presentation component 220 is concurrently compliant with an illumination mode of illumination component 240, and that enclosure 210 is in an operable configuration. In response to determining that there is concurrent compliance among the set of compliance rules, in an aspect, compliance component 212 can enable release of optical energy for interrogation of the sample. This aspect can reduce opportunities for accidental release of laser energy, for example, where the enclosure is not properly closed, where the probe is not in proper position/contact with the sample, etc. Moreover, this aspect can act as a trigger, such that the compliance rules of the group define when an interrogation of the sample can begin. In another aspect, the compliance rules can benefit the analysis by determining the presence of conditions that are beneficial to improved operation of the Raman spectrometer, e.g., by determining that the illumination source is off before allowing the laser to fire on the sample, compliance component 212 removes ambient light in the enclosure that could interfere with the analysis. In a further aspect, compliance component 212 can disable the release of optical energy in response to determining that a rule has gone into noncompliance, e.g., compliance component 212 can determine that there is no longer concurrent compliance and, accordingly, can stop enabling release of optical energy.

Figure 3:
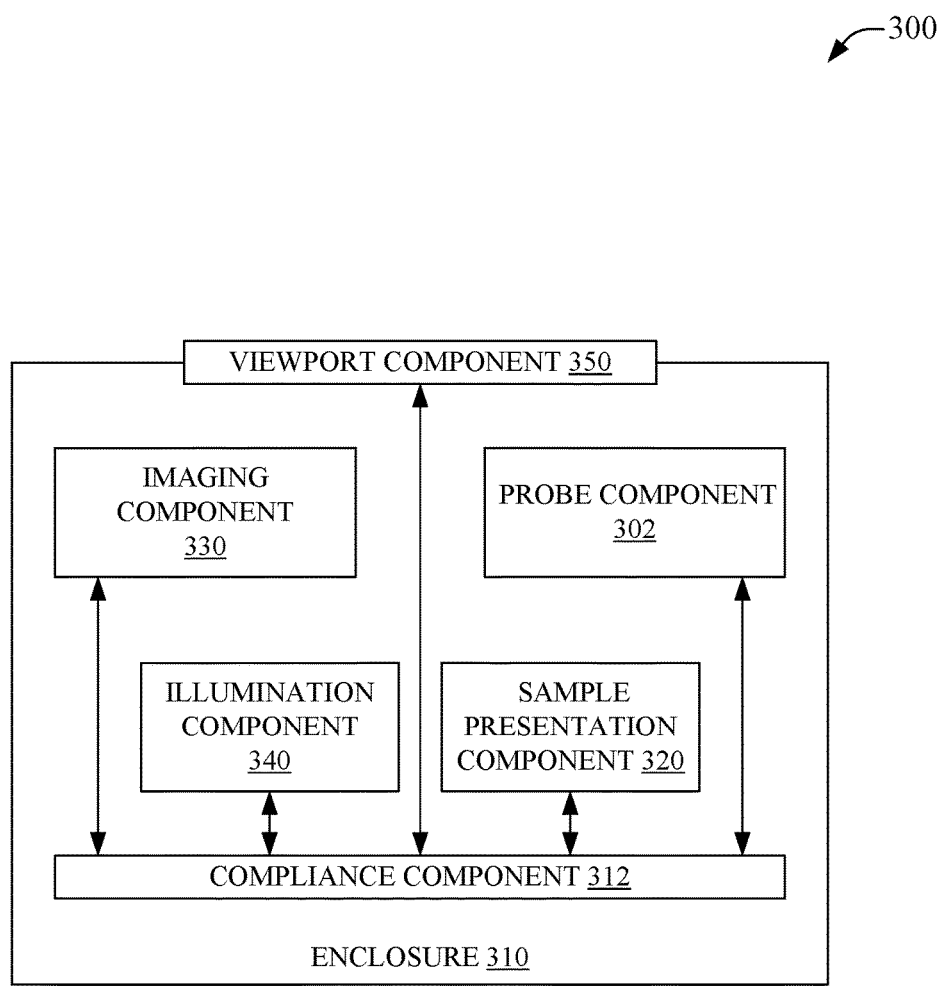
FIG. 3 illustrates an example system that facilitates direct monitoring of a sample to probe interface of an optical analytical instrument comprising an enclosure in accordance with aspects of the subject disclosure.

FIG. 3 illustrates a system 300 that facilitates direct monitoring of a sample to probe interface of an optical analytical instrument comprising an enclosure in accordance with aspects of the subject disclosure. System 300 can comprise enclosure 310. Enclosure 310 can enclose an interface between a sample and an analytical instrument. In an embodiment, enclosure 310 can enclose probe component 302, sample presentation component 320, imaging component 330, and illumination component 340. Probe component 302, sample presentation component 320, imaging component 330, and illumination component 340 can be communicatively coupled to compliance component 312.

In an embodiment, probe component 302 can comprise an optical element to direct optical energy at a sample. In an embodiment, the optical element that directs optical energy at a sample can comprise a spherical optical element. A spherical optical element can be a BallProbe® that can enable Raman spectrometry via probe component 302. An example benchtop analytical device comprising probe component 302 can perform Raman spectrometry by dipping or inserting a portion of probe component 302 into a sample, against a sample, etc., and initiating an optical interrogation of said sample. In an aspect, probe component 302 can move relative to sample presentation component 320, e.g., in the x-axis, y-axis, z-axis, rotationally, etc., so as to be able to access different portions of a sample, different samples, etc., for analysis. Moreover, in some embodiments, motion of probe component 302 can be in addition to, or in lieu of, motion by sample presentation component 320.

In some embodiments, sample presentation component 320 can present a sample for interrogation via probe component 302. In an aspect, sample presentation component 320 can move relative to probe component 302, e.g., in the x-axis, y-axis, z-axis, rotationally, etc., so as to be able to present different portions of a sample, different samples, etc., for analysis via probe component 302. As previously noted, in some embodiments, motion of sample presentation component 320 can be in addition to, or in lieu of, motion by probe component 302. A relative position between sample presentation component 320 and probe component 302 can be determined, e.g., via compliance component 312, via sample presentation component 320, via a connected controller/computer, etc. The relative position can be employed to determine that the sample is appropriately oriented for optical interrogation. In some embodiments, sample presentation component 320 can comprise a liquid flow cell, a gas flow cell, a sample stage, etc. In some example embodiments, sample presentation component 320 can comprise a multi-well plate, e.g., a 384-, 96-, 48-, 24-, 12-, 6-well plate sample container, etc. This can enable analysis of samples in one or more wells of the multi-well plate.

Imaging component 330 and illumination component 340 can enable remote viewing of the interior of enclosure 310, more particularly a sample and the orientation of the sample and probe component 302 as facilitated by positioning of the sample presentation component 320 and probe component 302. In an aspect, imaging component 330 and/or illumination component 340 can illuminate and/or image the presentation of the sample to probe component 302 in the human visible spectrum. In some embodiments, imaging component 330 and illumination component 340 can also illuminate and image the presentation of the sample to probe component 302 in spectrum outside of the normal range of human vision, e.g., UV, IR, etc. Moreover, imaging component 330 and illumination component 340 can be communicatively coupled to compliance component 312. This can enable compliance component 312 to determine the state of imaging component 330 and a state of illumination component 340 with regard to compliance rules for system 300.

Enclosure 310 can provide separation between the interior and exterior of enclosure 310, such that optical energy associated with interrogation of a sample is safely contained on the interior of enclosure 310, and that conditions external to enclosure 310 are less likely to interfere with the interrogation of the sample on the interior of enclosure 310. This can improve operator safety by blocking or attenuating optical emissions. Moreover, the enclosure can reduce ambient light entering the interface that can cause errors in an optical interrogation of a sample. In some embodiments, enclosure 310 can comprise optical attenuation features, e.g., paint, materials, and structures that absorb or attenuate ambient light.

Enclosure 310 can comprise viewport component 350. Viewport component 350 can be communicatively coupled to compliance component 312. Viewport component 350 can comprise an opening in enclosure 310 that can allow for direct viewing into the interior of enclosure 310. In an aspect, the opening can comprise window materials to allow a direct view into the interior of enclosure 310 while maintaining the integrity of enclosure 310 with regard to other features, e.g., environmental control, venting, limiting release of laser light frequencies, etc. As an example, viewport component 350 can comprise a laser safe window to attenuate laser light that can escape the sample interface. As another example, viewport component 350 can comprise a shutter, sliding plate, etc., that can physically block light transmission. In this example, the operator can directly view the sample, for example to position it, then can provide an input, e.g., slide the shutter shut, press a start button, etc., that can cause the shutter to close before the analysis can proceed. Whereas compliance component 312 can enable the release of the laser energy when the shutter is closed, the action of shuttering can, in effect, also cause the laser to fire on the sample. Viewport component 350 can, in some embodiments, be employed in conjunction with imaging component 330, e.g., allowing for visualization in the visible spectrum via viewport component 350 and in the IR, UV, etc., spectrum via imaging component 330. In other embodiments, imaging component 330 can be excluded where viewport component 350 is included.

Compliance component 312 can be communicatively coupled to one or more of the enclosure 310, probe component 302, sample presentation component 320, imaging component 330, illumination component 340, viewport component 350, etc. Compliance component 312 can receive a compliance rule related to an aspect of system 300. Compliance component 312 can determine that the compliance rule has been satisfied. In an aspect, compliance component 312 can determine concurrent compliance with a group of compliance rules related to aspects of system 300. As an example, compliance component 312 can determine that the position of probe component 302 relative to sample presentation component 320 is concurrently compliant with a viewport component 350 indicating closed, and that enclosure 310 is in an operable configuration. In response to determining that there is concurrent compliance among the set of compliance rules, in an aspect, compliance component 312 can enable release of optical energy for interrogation of the sample. This aspect can reduce opportunities for accidental release of laser energy, for example, where viewport component 350 is not properly closed, where the probe is not in proper position/contact with the sample, etc. Moreover, this aspect can act as a trigger, such that the compliance rules of the group define when an interrogation of the sample can begin. In another aspect, the compliance rules can benefit the analysis by determining the presence of conditions that are beneficial to improved operation of the Raman spectrometer, e.g., by determining that the illumination source is off before allowing the laser to fire on the sample, compliance component 312 assures that ambient light in the enclosure has diminished. In a further aspect, compliance component 312 can disable the release of optical energy in response to determining that a rule has gone into non-compliance, e.g., compliance component 312 can determine that there is no longer concurrent compliance and, accordingly, can stop enabling release of optical energy.

Figure 4:
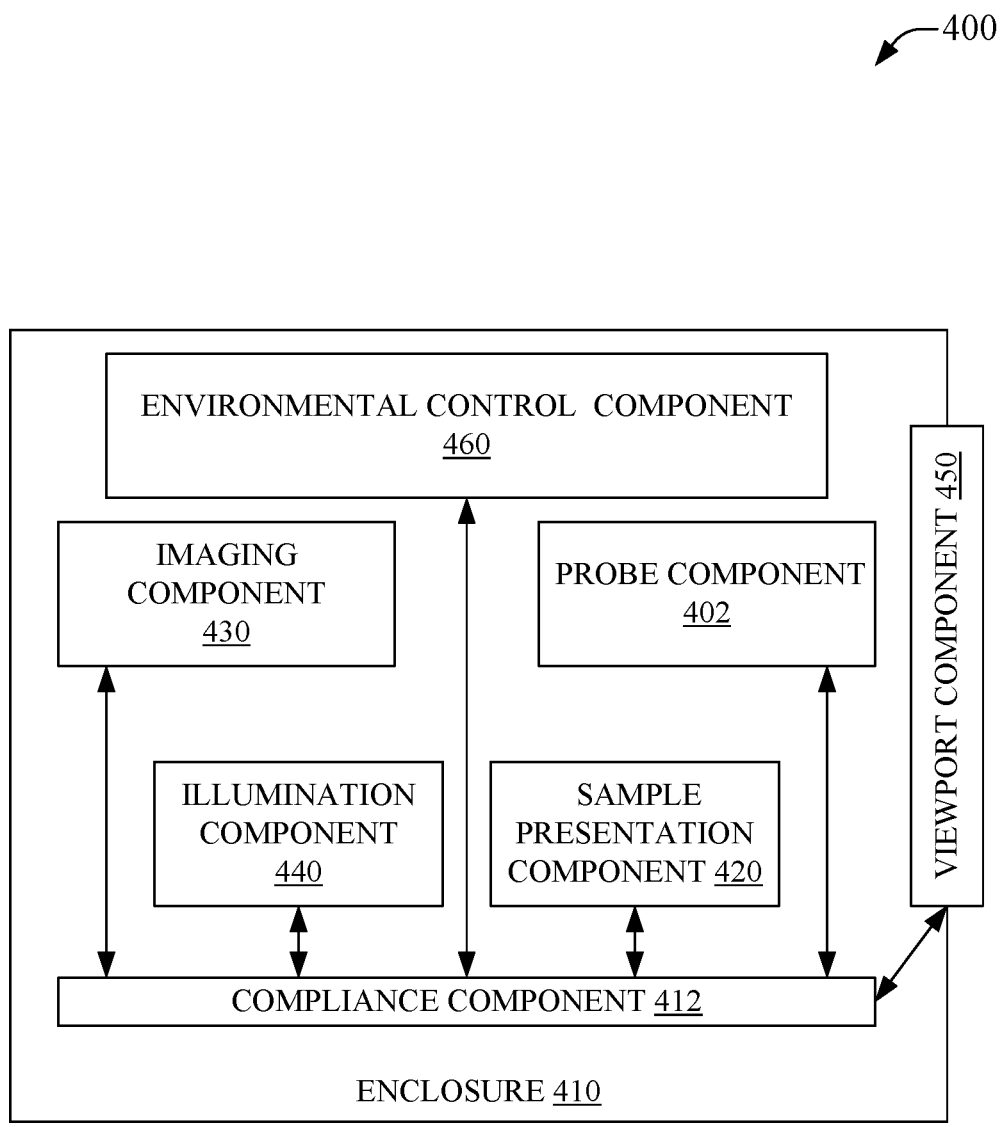
FIG. 4 illustrates an example system enabling environmental control within an enclosed optical analysis instrument in accordance with aspects of the subject disclosure.

FIG. 4 illustrates a system 400 enabling environmental control within an enclosed optical analysis instrument in accordance with aspects of the subject disclosure. System 400 can comprise enclosure 410. Enclosure 410 can enclose an interface between a sample and an analytical instrument. In an embodiment, enclosure 410 can enclose probe component 402, sample presentation component 420, imaging component 430, and illumination component 440. Probe component 402, sample presentation component 420, imaging component 430, and illumination component 440 can be communicatively coupled to compliance component 412.

In an embodiment, probe component 402 can comprise an optical element to direct optical energy at a sample. In an embodiment, the optical element that directs optical energy at a sample can comprise a spherical optical element. A spherical optical element can be a BallProbe® that can enable Raman spectrometry via probe component 402. An example benchtop analytical device comprising probe component 402 can perform Raman spectrometry by dipping or inserting a portion of probe component 402 into a sample, against a sample, etc., and initiating an optical interrogation of said sample. In an aspect, probe component 302 can move relative to sample presentation component 320, e.g., in the x-axis, y-axis, z-axis, rotationally, etc., so as to be able to access different portions of a sample, different samples, etc., for analysis.

In an embodiment, sample presentation component 420 can present a sample for interrogation via probe component 402. In an aspect, sample presentation component 420 can move relative to probe component 402, e.g., in the x-axis, y-axis, z-axis, rotationally, etc., so as to be able to present different portions of a sample, different samples, etc., for analysis via probe component 402. A position of sample presentation component 420 and probe component 402 can be determined. The position can be employed to determine that the sample is appropriately oriented for optical interrogation. In some embodiments, sample presentation component 420 can comprise a liquid flow cell, a gas flow cell, a sample stage, etc. In some example embodiments, sample presentation component 420 can comprise a multi-well plate. This can enable analysis of samples in one or more wells of the multi-well plate.

In an embodiment, system 400 can comprise environmental control component 460. Environmental control component 460 can enable control of an environment within enclosure 410. Environmental control component 460 can be communicatively coupled to compliance component 412. This can facilitate analysis of delicate samples, hazardous samples, etc. As an example, environmental control component 360 can maintain a temperature within enclosure 410, e.g., below freezing, to allow analysis of icy samples, at STP to allow analysis to be performed independent of temperature or pressure variation, etc. As another example, environmental control component 460 can vent the enclosure to a fume hood, scrubber or other filtration, etc. As a further example, environmental control component 460 can control humidity. In a still further example, environmental control component 460 can maintain a gaseous environment within enclosure 410, for example, an inert environment, a reactive environment, etc. In addition, environmental component 460 can control aspects of other components of system 400, for example, controlling a hot-plate or cold-plate feature of sample presentation component 420, control of a stir-plate motion for a stir-plate enabled sample presentation component 420, control of illumination component 440 to, for example, UV sterilize the internal area of enclosure 410, etc.

Enclosure 410 can provide separation between the interior and exterior of enclosure 410, such that optical energy associated with interrogation of a sample is safely contained on the interior of enclosure 410, and that conditions external to enclosure 410 are less likely to interfere with the interrogation of the sample on the interior of enclosure 410. This can improve operator safety by blocking or attenuating optical emissions. Moreover, the enclosure can reduce ambient light entering the interface that can cause errors in an optical interrogation of a sample. In some embodiments, enclosure 410 can comprise optical attenuation features, e.g., paint, materials, and structures that absorb or attenuate ambient light.

Enclosure 410 can comprise viewport component 450. Viewport component 450 can be communicatively coupled to compliance component 412. Viewport component 450 can comprise an opening in enclosure 410 that can allow for direct viewing into the interior of enclosure 410. In an aspect, the opening can comprise window materials to allow a direct view into the interior of enclosure 410 while maintaining the integrity of enclosure 410 with regard to other features, e.g., environmental control, venting, limiting release of laser light frequencies, etc.

Enclosure 410 can further enclose imaging component 430 and illumination component 440. Imaging component 430 and illumination component 440 can enable remote viewing of the interior of enclosure 410, more particularly a sample and the orientation of the sample and probe component 402 as facilitated by positioning of the sample presentation component 420 and probe component 402. In an aspect, imaging component 430 and illumination component 440 can illuminate and image the presentation of the sample to probe component 402 in the human visible spectrum. In some embodiments, imaging component 430 and illumination component 440 can also illuminate and image the presentation of the sample to probe component 402 in spectrum outside of the normal range of human vision, e.g., UV, IR, etc. Moreover, imaging component 430 and illumination component 440 can be communicatively coupled to compliance component 412. This can enable compliance component 412 to determine the state of imaging component 430 and illumination component 440 with regard to compliance rules for system 400. In some embodiments, illumination component 440 can further enable sterilization within enclosure 410, e.g., illumination component 440 can generate sufficient UV radiation to sterilize some, or all, of the interior of enclosure 410, etc. In some embodiments, a UV sterilization feature can be controlled by environmental control component 460.

Compliance component 412 can be communicatively coupled to one or more of the enclosure 410, probe component 402, sample presentation component 420, imaging component 430, illumination component 440, viewport component 450, environmental control component 460, etc. Compliance component 412 can receive a compliance rule related to an aspect of system 400. Compliance component 412 can determine that the compliance rule has been satisfied. In an aspect, compliance component 412 can determine concurrent compliance with a group of compliance rules related to aspects of system 400. As an example, compliance component 412 can determine that the position of probe component 402 relative to sample presentation component 420 is concurrently compliant with an illumination mode of illumination component 440, an internal inter gas environment via environmental control component 460, and that enclosure 410 is in an operable configuration. In response to determining that there is concurrent compliance among the set of compliance rules, in an aspect, compliance component 412 can enable release of optical energy for interrogation of the sample. This aspect can reduce opportunities for accidental release of laser energy, for example, where the enclosure is not properly closed, where the probe is not in proper position/contact with the sample, etc. Moreover, this aspect can act as a trigger, such that the compliance rules of the group define when an interrogation of the sample can begin. In another aspect, the compliance rules can benefit the analysis by determining the presence of conditions that are beneficial to improved operation of the Raman spectrometer. As an example, by determining that the illumination source is off before allowing the laser to fire on the sample, compliance component 412 removes ambient light in the enclosure that could interfere with the analysis. As another example, by determining that the sample is in a stable predetermined temperature, via environmental control component 460, the captured spectral data can be more consistent than for data captured at varying temperatures. In a further aspect, compliance component 412 can disable the release of optical energy in response to determining that a rule has gone into non-compliance, e.g., compliance component 412 can determine that there is no longer concurrent compliance and, accordingly, can stop enabling release of optical energy.

Figure 5:
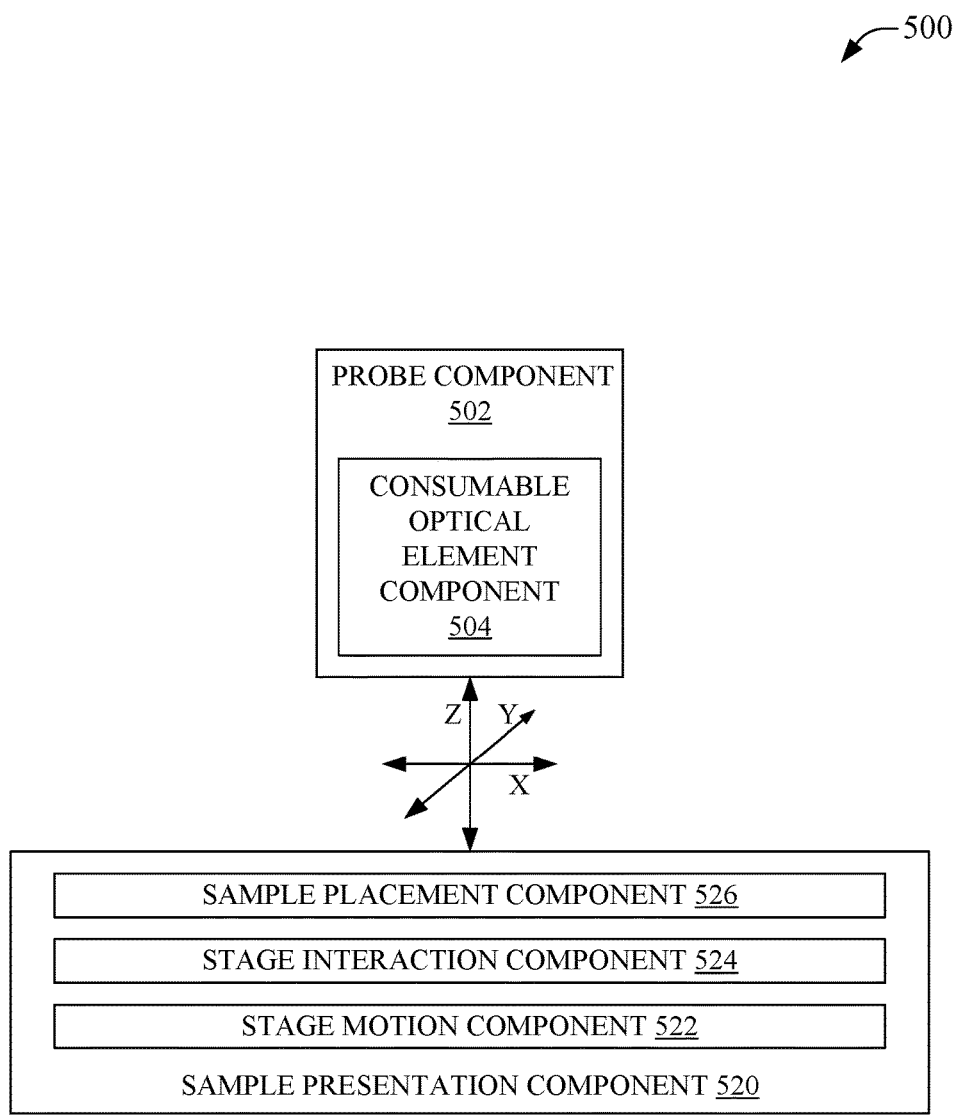
FIG. 5 illustrates an example system that facilitates translation of a sample stage for an enclosed optical analysis instrument in accordance with aspects of the subject disclosure.

FIG. 5 illustrates a system 500 that facilitates translation of a sample stage for an enclosed optical analysis instrument in accordance with aspects of the subject disclosure. System 500 can comprise probe component 502 and sample presentation component 520. Probe component 502 and sample presentation component 520 can move relative to each other, e.g., in the x-, y-, and z-planes, rotationally, etc. This can allow a sample to be positioned relative to probe component 502 to enable optical analysis, e.g., Raman spectroscopy, IR spectroscopy, UV-Vis spectroscopy, etc., at determined locations of the sample. In another aspect, where sample presentation component 520 comprises a plurality of samples, these samples can be positioned relative to probe component 502 to enable optical analysis of one or more of the plurality of samples.

In an embodiment, probe component 502 can comprise an optical element to direct optical energy at a sample. In an embodiment, the optical element that directs optical energy at a sample can comprise a spherical optical element. A spherical optical element can be a BallProbe® that can enable Raman spectrometry via probe component 502. An example benchtop analytical device comprising probe component 502 can perform Raman spectrometry by dipping or inserting a portion of probe component 502 into a sample, against a sample, etc., and initiating an optical interrogation of said sample. In an aspect, probe component 502 can move relative to sample presentation component 520, e.g., in the x-axis, y-axis, z-axis, rotationally, etc., so as to be able to access different portions of a sample, different samples, etc., for analysis.

In some embodiments, probe component 502 can comprise consumable optical element component 504. In an aspect, consumable optical element component 504 can comprise the optical element to direct optical energy at the sample. As an example, consumable optical element component 504 can be a disposable tip with a spherical optical element that is connected to probe component 502. As such, when consumable optical element component 504 becomes dirty, damaged, ill suited to the determined optical analysis, etc., consumable optical element component 504 can be jettisoned and a replacement consumable optical element component 504 can be connected to probe component 502 to proceed with further analysis. As an example, disposable pipette tips can be analogous to consumable optical element component 504, in that much as a disposable pipette tip can be used repeatedly, there are situations in which replacement of the disposable pipette tip is desirable, e.g., to prevent cross contamination, damage to the tip, fouling of the tip, etc. Similarly, consumable optical element component 504 can allow continued use of an optical element until it is determined that the consumable optical element component 504 should be replaced with another consumable optical element component 504. In an aspect, the replacement consumable optical element component 504 can be the same, similar to, or different from, the consumable optical element component 504 being replaced.

Moreover, in some embodiments, consumable optical element component 504 can be constructed of nearly any material. Consumable optical element component 504 can comprise a suitable polymer. Consumable optical element component 504 can comprise other materials, such as, but not limited to, stainless steel, gold, or other metal; borosilicate or other glass; starches or other carbohydrates, etc.; or nearly any other material suitable to a particular sample environment. Moreover, materials can be machined, sintered, cast, injection molded, 3D-printed, etc., for example to form a body, optical element seat, shroud, etc., of consumable optical element component 504. As an example, consumable optical element component 504 can comprise a polymer body having a sufficiently high coefficient of friction to allow it to be retained by a friction press fit on a receiving end of probe component 502. In another aspect, some embodiments of consumable optical element component 504 can comprise an optical element that can be generally spherical. The optical element can be separately manufactured and added to the body of consumable optical element component 504, either as part of a molding process, bonded with an adhesive, attached with a friction or press fit, mechanically captured, etc. In other embodiments, the spherical optical element can be co-formed with the body as part of a molding process, e.g., the spherical optical element can be formed, of the same or a different material, as the consumable optical element component 504 body, such as by injection molding; can be formed, of the same or a different material, as the consumable optical element component 504 via 3D printing; etc. Additionally, spherical optical elements can be manufactured from nearly any appropriate material, including the same or different materials as the body of consumable optical element component 504. Non-limiting examples of appropriate materials can include a polymer, glass, mineral, etc., depending on the optical properties suited to a given scenario. As noted herein above, 'spherical' optical element, or similar terms, can refer to an optical element, e.g., a lens, etc., that has a spherical, or nearly spherical, geometry. Moreover, the term 'spherical optical element,' as used herein, can also include any optical element that conducts light via a portion of an optical element that comprises a curved surface approximating at least a portion of a sphere. As an example, an optical element comprising two individual generally hemispherical portions can also be considered a spherical element within the scope of the instant disclosure.

In an embodiment, sample presentation component 520 can present a sample for interrogation via probe component 502. In an aspect, sample presentation component 520 can move relative to probe component 502, e.g., in the x-axis, y-axis, z-axis, rotationally, etc., so as to be able to present different portions of a sample, different samples, etc., for analysis via probe component 502. A position of sample presentation component 520 and probe component 502 can be determined. The position can be employed to determine that the sample is appropriately oriented for optical interrogation. In some embodiments, sample presentation component 520 can comprise a liquid flow cell, a gas flow cell, a sample stage, etc. In some example embodiments, sample presentation component 520 can comprise a multi-well plate. This can enable analysis of samples in one or more wells of the multi-well plate.

Movement of sample presentation component 520 can be enabled by stage motion comp 522. In an aspect, stage motion comp 522 can comprise, for example, servo motors, piezo-electric actuators, etc., allowing movement of sample placement component 526. Sample placement component 526 can facilitate positioning of a sample in a location that can be treated as static in regard to a reference point of sample presentation component 520, such that motion of sample presentation component 520 can be correlated with motion of the sample positioned by sample placement component 526. In an aspect, sample placement component 526 can comprise a multi-well plate, a flow cell for a gas and/or liquid, mechanical gripper assembly, an adhesive, a suction gripper assembly, etc., allowing for placement of a sample that is in at least one of a solid, liquid, or gas phase, such that sample presentation component 520 can present the sample to probe component 502 for optical analysis. As an example, a chunk of rock can be adhered to a sample stage, e.g., sample placement component 526, via a piece of double sided tape, allowing stage motion component 522 to move the rock into position relative to the position/movement of probe component 502 to enable a spherical optic of consumable optical element 504 to pass laser light onto a desired portion of the rock for Raman analysis thereof. Moreover, sample presentation component 520 can comprise stage interaction component 522 that can determine interaction between the probe component 502 and the sample. In an aspect, stage interaction component 522 can determine when probe component 502 comes into contact with a sample, is located at a determined distance into a sample, e.g., a liquid or gas sample into which probe component 502 is dipped, etc., is at a determined angle to the sample, etc. As an example, where a BallProbe® equipped consumable optical element component 504 is used for contact Raman analysis, the BallProbe® tip can be brought into physical contact with the sample. Stage interaction component 524 can determine when contact has occurred. This determined contact can be employed by a compliance component, e.g., 112, 212, 312, 412, etc., to aid in determining concurrent satisfaction of compliance rules. Moreover, This determined contact can be employed to stop additional motion between probe component 502 and sample presentation component 520 that could damage the BallProbe® optical element, e.g., crushing it via additional pressure, scratching it by lateral motion while the BallProbe® is in contact with a solid sample, etc. As an example, a spring-biased pressure sensor can determine contact has been made without exceeding the bias pressure exerted by the bias spring. As another example, an ultrasonic proximity sensor can be employed to determine a distance between the sample presentation component 520 and probe component 502, which can be used with a model to determine a distance of the probe tip to/into the sample. Numerous other examples are readily appreciated by one of skill in the art and all such examples are within the scope of the present disclosure despite not being explicitly recited for the sake of clarity and brevity.

Figure 6:
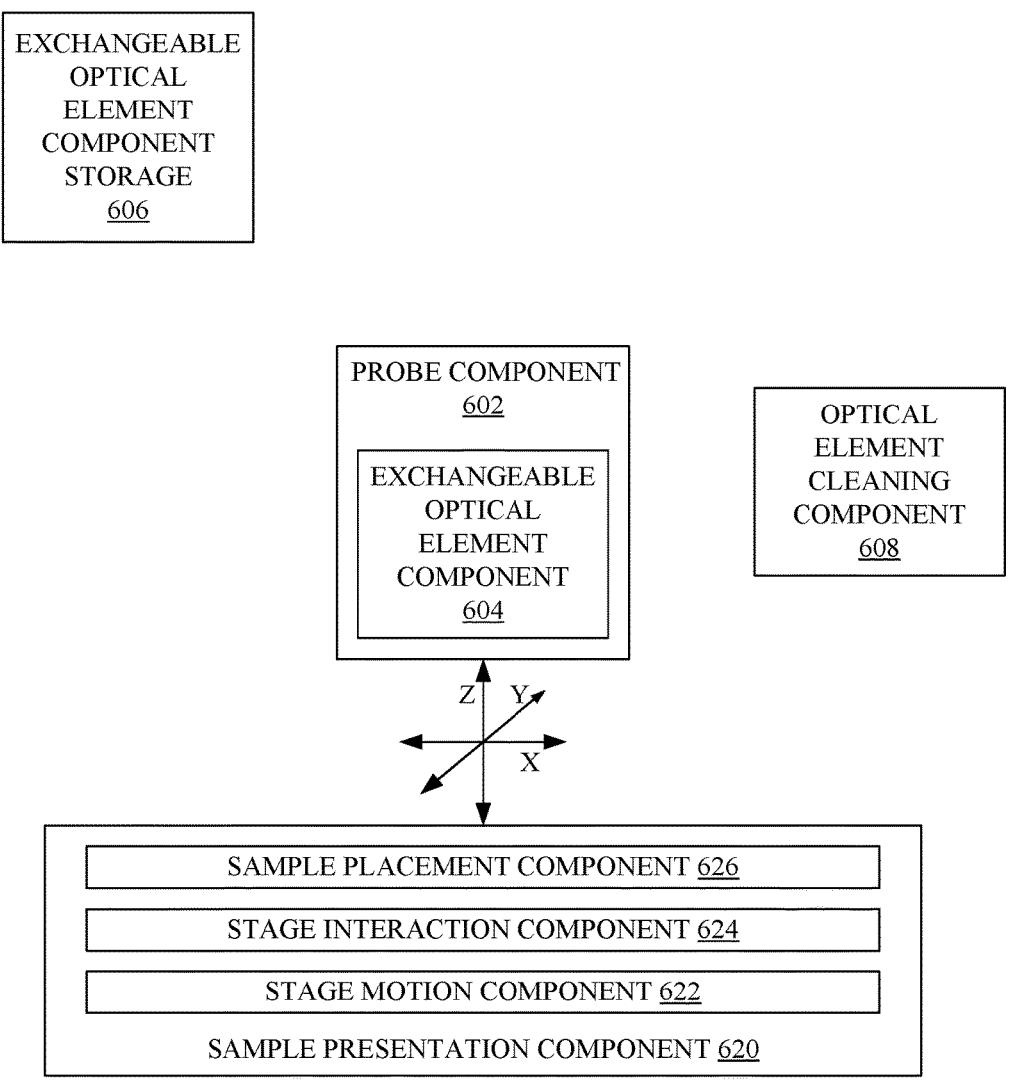
FIG. 6 illustrates an example system enabling cleaning or replacement of an exchangeable optical element component of a probe for an enclosed optical analysis instrument in accordance with aspects of the subject disclosure.

FIG. 6 illustrates a system 500 that facilitates cleaning or replacement of an exchangeable optical element component of a probe for an enclosed optical analysis instrument in accordance with aspects of the subject disclosure. System 600 can comprise probe component 602 and sample presentation component 620. Probe component 602 and sample presentation component 620 can move relative to each other, e.g., in the x-, y-, and z-planes, rotationally, etc. This can allow a sample to be positioned relative to probe component 602 to enable optical analysis at determined locations of the sample. In another aspect, where sample presentation component 620 comprises a plurality of samples, these samples can be positioned relative to probe component 602 to enable optical analysis of one or more of the plurality of samples.

In an embodiment, probe component 602 can comprise an optical element to direct optical energy at a sample. In an embodiment, the optical element that directs optical energy at a sample can comprise a spherical optical element. A spherical optical element can be a BallProbe® that can enable Raman spectrometry via probe component 602. An example benchtop analytical device comprising probe component 602 can perform Raman spectrometry by dipping or inserting a portion of probe component 602 into a sample, against a sample, etc., and initiating an optical interrogation of said sample. In an aspect, probe component 602 can move relative to sample presentation component 620, e.g., in the x-axis, y-axis, z-axis, rotationally, etc., so as to be able to access different portions of a sample, different samples, etc., for analysis.

In some embodiments, probe component 602 can comprise exchangeable optical element component 604. In an aspect, exchangeable optical element component 604 can comprise the optical element to direct optical energy at the sample. As an example, exchangeable optical element component 604 can be an exchangeable tip with a spherical optical element that is connected to probe component 602. As such, when exchangeable optical element component 604 becomes dirty, damaged, ill suited to the determined optical analysis, etc., a first exchangeable optical element component 604 can be removed and a second exchangeable optical element component 604 can be attached to probe component 602 to proceed with further analysis.

In an aspect, this can enable different exchangeable optical element components to be rotated into use based on the characteristics of the several exchangeable optical element components. As an example, a first exchangeable optical element component can have a sapphire lens and a second exchangeable optical element component can have a plastic lens. The second exchangeable optical element component can be used in conditions that do not require the sapphire lens of the first exchangeable optical element component, e.g., because damage to the plastic lens is less costly than to the sapphire lens), however, where an analysis is determined to be better suited to use of the sapphire lens, the second exchangeable optical element component can be exchanged for the first exchangeable optical element component. After the analysis with the sapphire lens is performed, the first exchangeable optical element component can be re-exchanged for the second exchangeable optical element component.

Moreover, in some embodiments, system 600 can comprise exchangeable optical element component storage 606. Exchangeable optical element component storage 606 can store exchangeable optical element component(s) that can be exchanged for exchangeable optical element component 604. In an aspect, exchangeable optical element component storage 606 can store a supply of disposable or consumable optical element components. In another aspect, exchangeable optical element component storage 606 can store other exchangeable optical element components. As an example, a modern computer numerical control CNC milling machine can be equipped with a turret system allowing rapid and automated exchange of milling machining tools, similarly, exchangeable optical element component storage 606 can allow for the rapid and automated exchange of exchangeable optical element components within an enclosure, e.g., 110-410, etc.

In some embodiments, probe component 602 can employ optical element cleaning component 608 to clean optical elements of probe component 602. In some embodiments, optical element cleaning component 608 can validate that the optical element of probe component 602 is clean, e.g., via calibration, intensity correction, flat-fielding techniques, wavelength registration techniques, etc. As an example, optical element cleaning component 608 can sonicate a probe tip dipped in a solvent between analytical runs where Raman spectra is being taken on oil samples, which can rinse the oil from the probe tip, e.g., the optical element in contact with the oil can be cleaned, to allow an exchangeable optical element component 604 to be reused. The cleanliness of the optical element can be verified before reuse. Where the cleanliness of the optical element fails, the optical element can be re-cleaned and validated or, in some embodiments, exchanged for a replacement exchangeable optical element component 604.

In some embodiments, exchangeable optical element component 604 can be constructed of nearly any material. Exchangeable optical element component 604 can comprise a suitable polymer. Exchangeable optical element component 604 can comprise other materials, such as, but not limited to, stainless steel, gold, or other metal; borosilicate or other glass; starches or other carbohydrates, etc.; or nearly any other material suitable to a particular sample environment. Moreover, materials can be machined, sintered, cast, injection molded, 3D-printed, etc., for example to form a body, optical element seat, shroud, etc., of exchangeable optical element component 604. In another aspect, some embodiments of exchangeable optical element component 604 can comprise an optical element that can be generally spherical. Additionally, spherical optical elements can be manufactured from nearly any appropriate material, including the same or different materials as the body of exchangeable optical element component 604. As noted herein above, spherical optical element, or similar terms, can refer to an optical element, e.g., a lens, etc., that has a spherical, or nearly spherical, geometry. Moreover, the term spherical optical element, as used herein, can also include any optical element that conducts light via a portion of an optical element that comprises a curved surface approximating at least a portion of a sphere.

In an embodiment, sample presentation component 620 can present a sample for interrogation via probe component 602. In an aspect, sample presentation component 620 can move relative to probe component 602, e.g., in the x-axis, y-axis, z-axis, rotationally, etc., so as to be able to present different portions of a sample, different samples, etc., for analysis via probe component 602. A position of sample presentation component 620 and probe component 602 can be determined. The position can be employed to determine that the sample is appropriately oriented for optical interrogation. In some embodiments, sample presentation component 620 can comprise a liquid flow cell, a gas flow cell, a sample stage, etc. In some example embodiments, sample presentation component 620 can comprise a multi-well plate. This can enable analysis of samples in one or more wells of the multi-well plate.

Movement of sample presentation component 620 can be enabled by stage motion comp 622. In an aspect, stage motion comp 622 can allowing movement of sample placement component 626. Sample placement component 626 can facilitate positioning of a sample in a location that can be treated as static in regard to a reference point of sample presentation component 620, such that motion of sample presentation component 620 can be correlated with motion of the sample positioned by sample placement component 626.

Moreover, sample presentation component 620 can comprise stage interaction component 622 that can determine interaction between the probe component 602 and the sample. In an aspect, stage interaction component 622 can determine when probe component 602 comes into contact with a sample, is located at a determined distance into a sample, e.g., a liquid or gas sample into which probe component 602 is dipped, etc., is at a determined angle to the sample, etc. This determined interaction can be employed by a compliance component, e.g., 112, 212, 312, 412, etc., to aid in determining concurrent satisfaction of compliance rules. Moreover, this determined interaction can be employed to stop additional motion between probe component 602 and sample presentation component 620.

Figure 7:
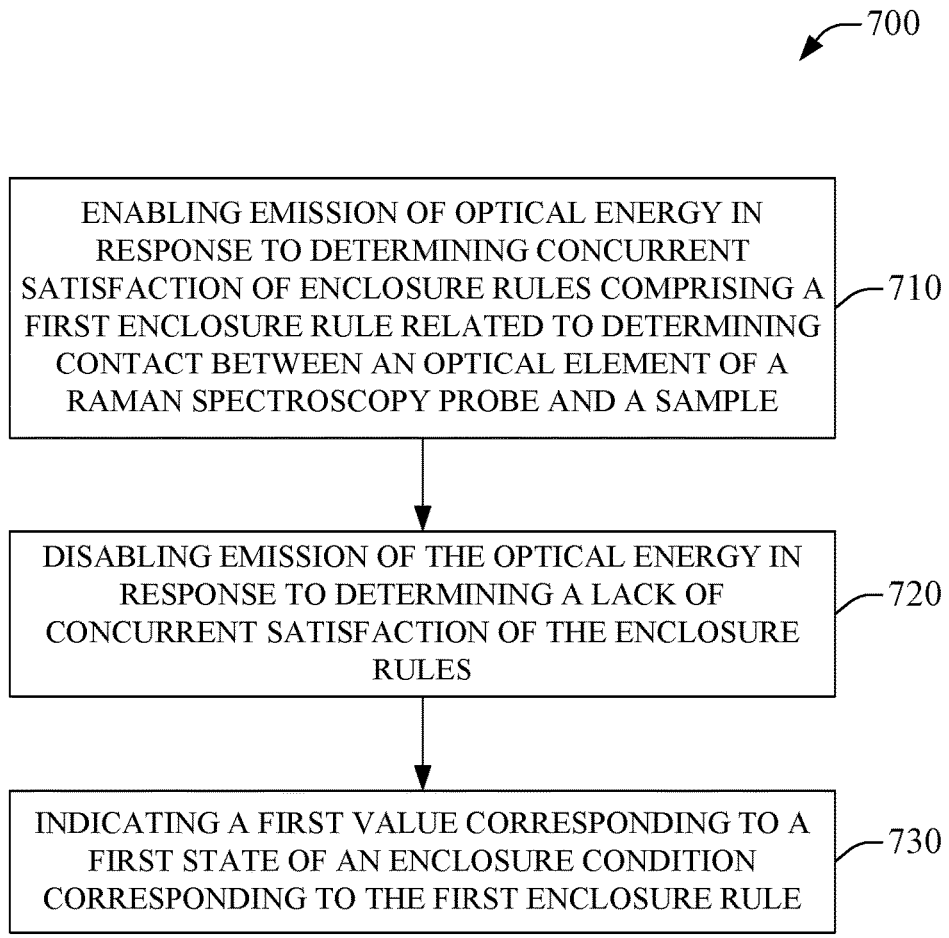
FIG. 7 depicts an example method facilitating release of optical interrogation energy based on satisfaction of enclosure rules for an enclosed optical analysis instrument in accordance with aspects of the subject disclosure.
Figure 8:
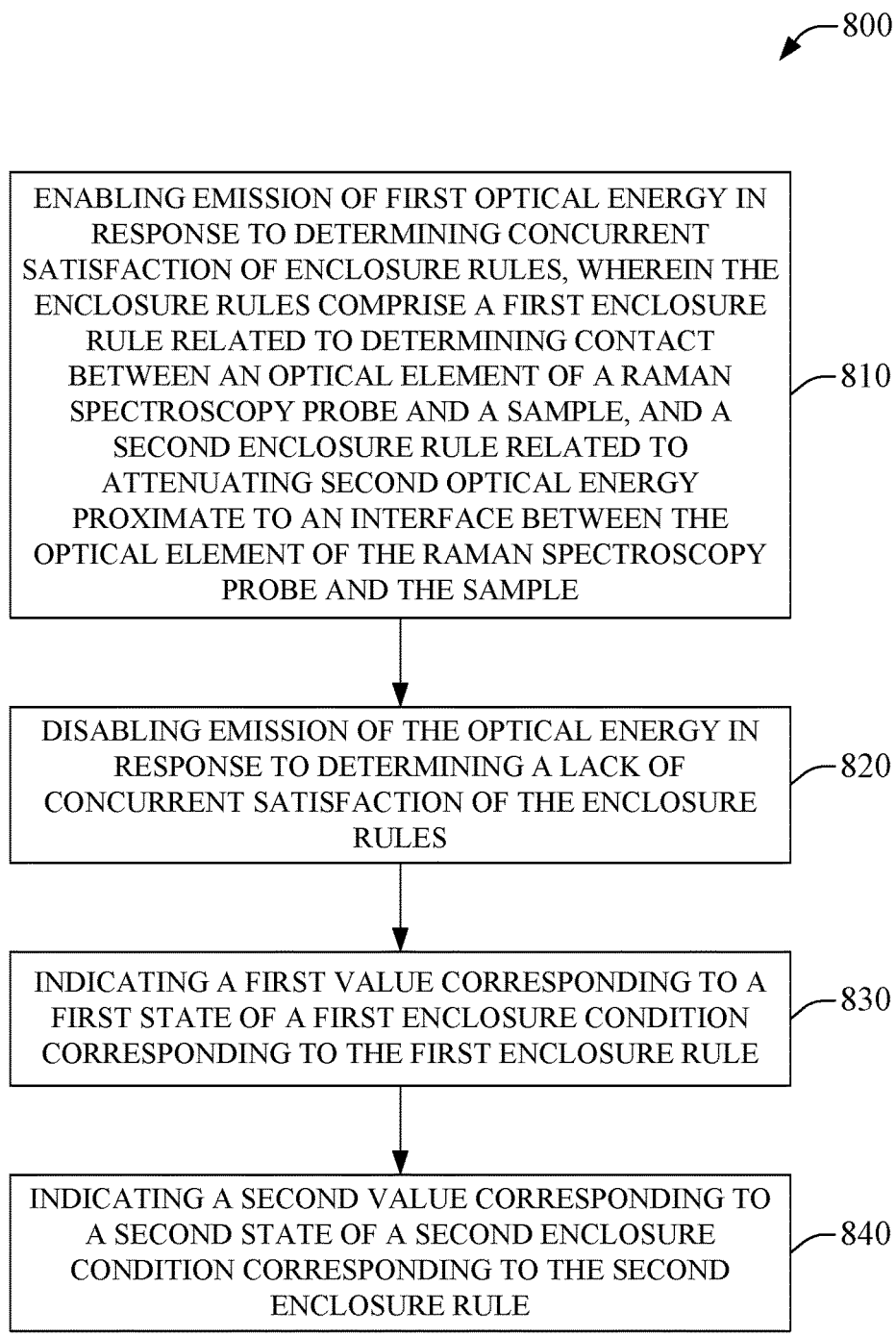
FIG. 8 illustrates an example method enabling emission of first interrogating optical energy based on an indication of contact between a probe and a sample and a concurrent indication of sufficiently attenuated non-interrogation optical energy in accordance with aspects of the subject disclosure.
Figure 9:
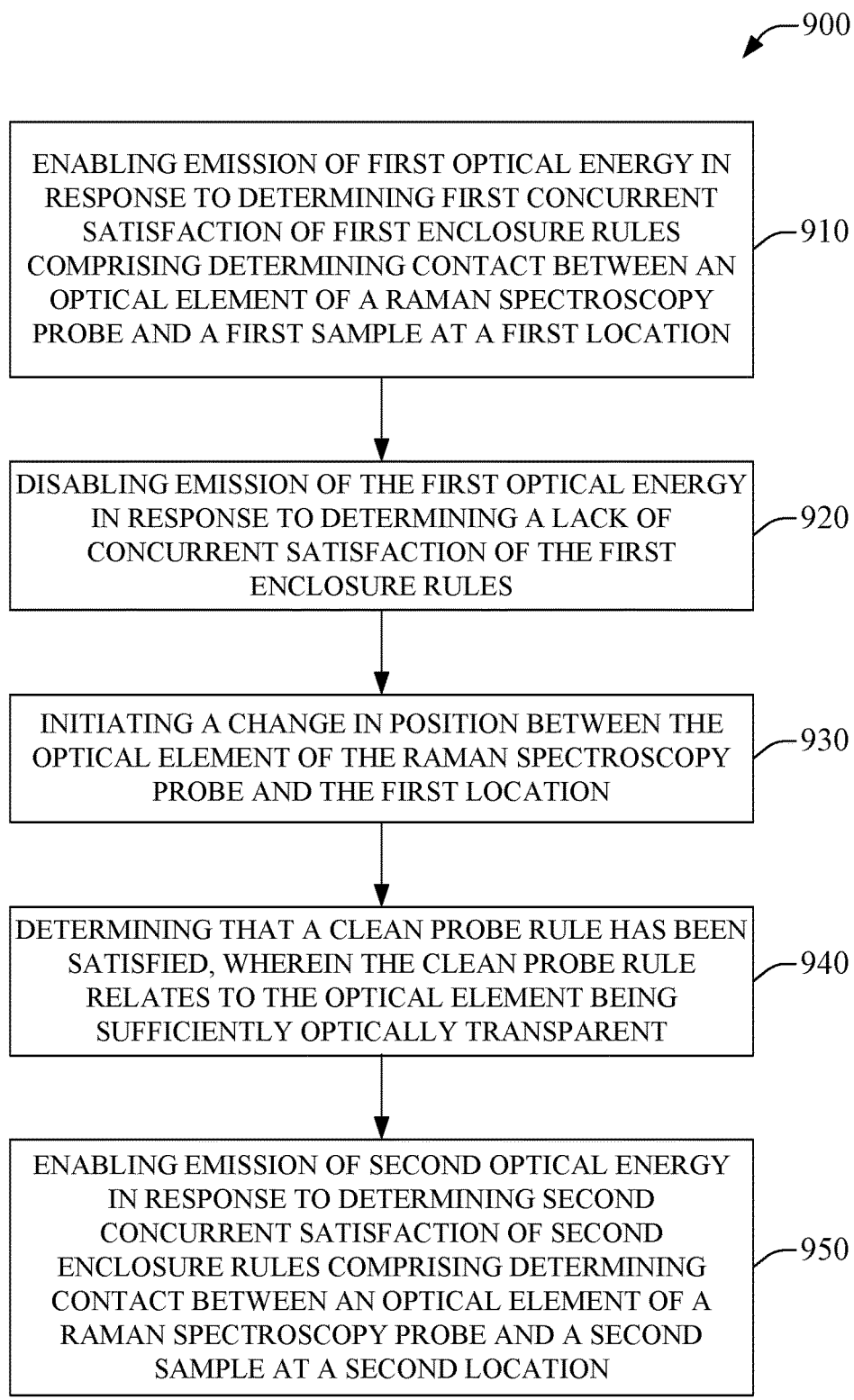
FIG. 9 illustrates an example method facilitating sequential optical interrogation of samples at different sample locations within an enclosed optical analysis instrument in accordance with aspects of the subject disclosure.

In view of the example system(s) described above, example method(s) that can be implemented in accordance with the disclosed subject matter can be better appreciated with reference to flowcharts in FIG. 7-FIG. 9. For purposes of simplicity of explanation, example methods disclosed herein are presented and described as a series of acts; however, it is to be understood and appreciated that the claimed subject matter is not limited by the order of acts, as some acts may occur in different orders and/or concurrently with other acts from that shown and described herein. For example, one or more example methods disclosed herein could alternatively be represented as a series of interrelated states or events, such as in a state diagram. Moreover, interaction diagram(s) may represent methods in accordance with the disclosed subject matter when disparate entities enact disparate portions of the methods. Furthermore, not all illustrated acts may be required to implement a described example method in accordance with the subject specification. Further yet, two or more of the disclosed example methods can be implemented in combination with each other, to accomplish one or more aspects herein described. It should be further appreciated that the example methods disclosed throughout the subject specification are capable of being stored on an article of manufacture (e.g., a computer-readable medium) to allow transporting and transferring such methods to computers for execution, and thus implementation, by a processor or for storage in a memory.

FIG. 7 illustrates a method 700 facilitating release of optical interrogation energy based on satisfaction of enclosure rules for an enclosed optical analysis instrument in accordance with aspects of the subject disclosure. At 710, method 700 can comprise enabling emission of optical energy. The enabling can be in response to determining concurrent satisfaction of enclosure rules comprising a first enclosure rule. The first enclosure rule can be related to determining contact between an optical element of a Raman spectroscopy probe and a sample.

In an aspect, a Raman spectrometer can interrogate a sample by emitting optical energy, into or onto a sample. Optical energy can be returned from the sample that is characteristic of the molecular composition of the sample. A first enclosure rule related to the contact can be determined to be satisfied when a probe, e.g., probe component 102, 202, 302, 420, 502, 602, etc., is in contact with a sample, e.g., is pressed against a solid sample, inserted into a liquid or gas sample, etc. Where this first enclosure rule is part of a group of enclosure rules, and the group of enclosure rules is determined to be concurrently satisfied, the release of optical energy for interrogation of a sample can be enabled. In an aspect, this can allow designation of procedures, tolerances, and safety measures to be automatically monitored before allowing the analysis to proceed. As an example, a contact sensor can verify that an enclosure is closed before allowing a release of laser light to interrogate a sample, which can prevent the laser emission while the enclosure is not closed to protect an operator. As another example, a light sensor can be monitored to ensure the sample is in darkness before the analysis can proceed, which can reduce artifacts in the spectral results that can occur when ambient light is present. As a further example, a temperature within the enclosure can be monitored to allow a sample to be at a known state before the analysis is enabled to proceed, which can reduce variation between analytical runs that can result from operators opening and closing an enclosure between runs.

At 720, method 700 can comprise disabling emission of the optical energy in response to determining a lack of concurrent satisfaction of the enclosure rules. In an aspect, the optical energy can be stopped or shunted in response to determining that an enclosure rule of the enclosure rules is no longer satisfied. Between 710 and 720, this can result in releasing optical energy only when the enclosure rules are simultaneously satisfied. A compliance component, e.g., 112, 212, 312, 412, etc., can receive input from various sensors, monitors, user inputs, etc., to coordinate a release of a hold on optical energy to begin an analysis, e.g., the analysis can occur in response to the concurrent satisfaction of one or more compliance rules.

As an example, an operator can place a sample in an enclosure having an imaging system and a sample contact sensor. The example operator can then position a Raman probe at an area of interest on the sample. The imaging system can then be switched to a non-illumination mode to reduce light pollution and the example Raman probe can be advanced against the sample. In this example, the compliance component can determine that the enclosure is properly closed, that concurrently the illumination source is off, and can wait for the contact sensor to indicate concurrently that the Raman probe has contacted the sample. Upon the sample being contacted by the Raman probe, the contact sensor can indicate that contact has been made, which can satisfy a contact rule concurrently with the lights being off, and the enclosure being closed, and can result in the analysis being allowed to proceed, e.g., the concurrent satisfaction of the conditions can start the analysis. This can allow an operator to simply place the sample, close the door, position the sample via a camera, and move the probe to contact the sample, whereupon the analysis is triggered and the operator can begin the subsequent analysis. Further, when the probe is retracted from the sample, the enclosure is opened, or the illumination source is reactivated, the interrogation beam can be shut off. This can serve to protect the operator of the instrument, protect the optical sensor of the instrument, ensure data quality, etc. Moreover, an array of samples, e.g., placed on a 96-well plate, etc., can be placed in an embodiment of the disclosed subject matter, the enclosure can be closed, the operator can move, with the help of an internal video camera and illuminator, the probe to the first of the 96 wells in the plate and press a start button. In response, the example system can shut off the illuminator and begin a stage translation process to bring the probe into contact with each well of the 96-well plate sequentially. The example compliance controller can verify that the enclosure is closed, that the illuminator is off, and can enable the Raman interrogation laser only when the probe is determined to be in contact with the sample plate, e.g., at each well as the translation process cycles the probe contact with each well, concurrent with the illuminator being off and the enclosure being closed. As such, should the enclosure be opened, the compliance component can prevent the release of laser energy.

At 730, method 700 can comprise indicating a first value corresponding to a first state of an enclosure condition corresponding to the first enclosure rule. At this point method 700 can end. This can allow access to the first value by other systems/components, operators, etc. As an example, where the first rule relates to determining contact between the optical element of a Raman probe and the sample, the first value can be a distance between the probe and the sample, between the probe and the sample stage, a proximity metric of the probe to the sample, a depth of insertion of the probe into a flow cell, an amount of pressure measured between the probe and the sample stage, etc. The first value can guide additional actions, e.g., where the pressure between the probe and the sample plate transitions a threshold value, the distance between the probe and sample plate can be increased to prevent damage to the optical element of the probe, etc.

In some embodiments, acquisition of optical spectrums can be facilitated by method 700. In an embodiment, a wireless link between a mobile device or other user equipment and the enclosed benchtop Raman spectrometer can enable control of aspects of the enclosed benchtop Raman spectrometer, for example, allowing modification, creation, deletion, etc., of enclosure rules and/or groups of enclosure rules. In another embodiment, a wired link between a user equipment and the enclosed benchtop Raman spectrometer can similarly enable control of aspects of the enclosed benchtop Raman spectrometer.

FIG. 8 illustrates a method 800 enabling emission of first interrogating optical energy based on an indication of contact between a probe and a sample and a concurrent indication of sufficiently attenuated non-interrogation optical energy in accordance with aspects of the subject disclosure. At 810, method 800 can comprise enabling emission of optical energy. The enabling can be in response to determining concurrent satisfaction of enclosure rules comprising a first enclosure rule and a second enclosure rule. The first enclosure rule can be related to determining contact between an optical element of a Raman spectroscopy probe and a sample. The second enclosure rule can be related to second optical energy proximate to the interface between the optical element and the sample.

A first enclosure rule related to the contact can be determined to be satisfied when a probe, e.g., probe component 102, 202, 302, 420, 502, 602, etc., is in contact with a sample, e.g., is pressed against a solid sample, inserted into a liquid or gas sample, etc. The first enclosure rule can be satisfied when the probe is in contact with the sample to be tested. A second enclosure rule can relate to attenuation of ambient light in the interior of the enclosure. In an aspect, for example where the interior of the enclosure is monitored by an imaging device using an illuminator, e.g., 230/240, 330/340, 430/440, etc., it can be desirable to have the illuminator not emitting light that can be detected at the detector of the Raman spectrometer during interrogation of a sample. As such, the second rule can validate that the illuminator is off, that ambient light is below a threshold level, etc., within the enclosure, and more particularly at the sample-probe interface where stray light could affect spectroscopy results. Where this first enclosure rule is part of a group of enclosure rules, the second enclosure rule is part of the group of enclosure rules, and the group of enclosure rules is determined to be concurrently satisfied, the release of optical energy for interrogation of a sample can be enabled.

At 820, method 800 can comprise disabling emission of the optical energy in response to determining a lack of concurrent satisfaction of the enclosure rules. In an aspect, the optical energy can be stopped or shunted in response to determining that an enclosure rule, e.g., the first enclosure rule, the second enclosure rule, etc., of the enclosure rules is not being concurrently satisfied. This can result in releasing optical energy if, and only if, the group of enclosure rules are simultaneously satisfied. A compliance component, e.g., 112, 212, 312, 412, etc., can receive input from various sensors, monitors, user inputs, etc., to coordinate a release of a hold on optical energy to begin an analysis, e.g., the analysis can occur in response to the concurrent satisfaction of one or more compliance rules.

At 830, method 800 can comprise indicating a first value corresponding to a first state of a first enclosure condition corresponding to the first enclosure rule. This can allow access to the first value by other systems/components, operators, etc. As an example, where the first rule relates to determining contact between the optical element of a Raman probe and the sample, the first value can be a distance between the probe and the sample, between the probe and the sample stage, a proximity metric of the probe to the sample, a depth of insertion of the probe into a flow cell, an amount of pressure measured between the probe and the sample stage, etc. The first value can guide additional actions, e.g., where the pressure between the probe and the sample plate transitions a threshold value, the distance between the probe and sample plate can be increased to prevent damage to the optical element of the probe, etc.

At 840, method 800 can comprise indicating a second value corresponding to a second state of a second enclosure condition corresponding to the second enclosure rule. At this point method 800 can end. This can allow access to the second value by other systems/components, operators, etc. As an example, where the second rule relates to determining ambient optical energy within the enclosure, the second value can be a measure of optical energy at a time, a time value indicating a rate of optical energy attenuation, etc. The second value can guide additional actions, e.g., where UV light causes a sample to fluoresce to facilitate placement of the probe relative to the sample, the fluorescence can decrease at a measurable rate, which measurable rate can be reflected in the second value. As such, this example second value can be employed, for example, by a timing delay component, e.g., comprised in the compliance component, etc., to delay onset of an optical analysis to allow for the fluorescence to drop below a threshold level to improve the results of the acquired spectral information.

FIG. 9 illustrates a method 900 that facilitating sequential optical interrogation of samples at different sample locations within an enclosed optical analysis instrument in accordance with aspects of the subject disclosure. At 910, method 900 can comprise enabling emission of first optical energy. The enabling can be in response to determining concurrent satisfaction of first enclosure rules comprising determining contact between an optical element of a Raman spectroscopy probe and a sample at a first location. Contact can be determined to be satisfied when a probe, e.g., probe component 102, 202, 302, 420, 502, 602, etc., is in contact with a sample, e.g., is pressed against a solid sample, inserted into a liquid or gas sample, etc.

At 920, method 900 can comprise disabling emission of the optical energy in response to determining a lack of concurrent satisfaction of the first enclosure rules. In an aspect, the optical energy can be stopped or shunted in response to determining that the first enclosure rules are not being concurrently satisfied. This can result in releasing optical energy if, and only if, the first enclosure rules are simultaneously satisfied. A compliance component, e.g., 112, 212, 312, 412, etc., can receive input from various sensors, monitors, user inputs, etc., to coordinate a release of a hold on optical energy to begin an analysis, e.g., the analysis can occur in response to the concurrent satisfaction of one or more compliance rules of the first enclosure rules.

At 930, method 900 can comprise indicating a change in position between the optical element of the Raman spectroscopy probe and the first location. In an aspect, the change in position can occur subsequent to the probe not being in contact with a solid sample to prevent damage to the probe, although it will be noted that where the probe is in a gas or liquid, the change in position can occur without removing the probe form contact with the sample where the gas or liquid is unlikely to damage the probe. In an embodiment, the change in position can correlate to distances between wells comprised in a multi-well plate, e.g., a 384-, 96-, 48-, 24-, 12-, 6-well plate sample container, etc. This can enable analysis of samples in one or more wells of the multi-well plate.

At 940, method 900 can comprise determining that a clean probe rule has been satisfied. The clean probe rule can relate to cleaning of the optical element of the Raman spectroscopy probe between contacts with a sample(s), e.g., the optical element can be determined to be optically transparent in Raman relevant regions to satisfy the clean probe rule. In an embodiment, where cleaning of the probe fails, the probe can be exchanged for a new or otherwise clean probe. This new or other clean probe can satisfy the clean probe rule.

At 950, method 900 can comprise enabling emission of second optical energy. The enabling can be in response to determining concurrent satisfaction of second enclosure rules comprising determining contact between an optical element of a Raman spectroscopy probe and a sample at a second location. At this point method 900 can end. In an aspect, the second capture of a second Raman spectrum at a second location of a sample, or another sample, can occur automatically in response to the second enclosure rules being determined to be concurrently satisfied. In an example, where a probe is in contact with a sample in a first well of a plate, a first spectrum can be captured where the first enclosure rules are concurrently satisfied. Upon retracting the probe from the first well, the first enclosure rules can fail to be satisfied and the Raman laser can correspondingly be shunted. The plate can be moved and the probe can be cleaned. The probe can then be brought into contact with a sample in a second well of the plate in a manner that concurrently satisfies second enclosure rules, whereby shunting of the laser is ended and a second Raman spectrum can be captured.

Figure 10:
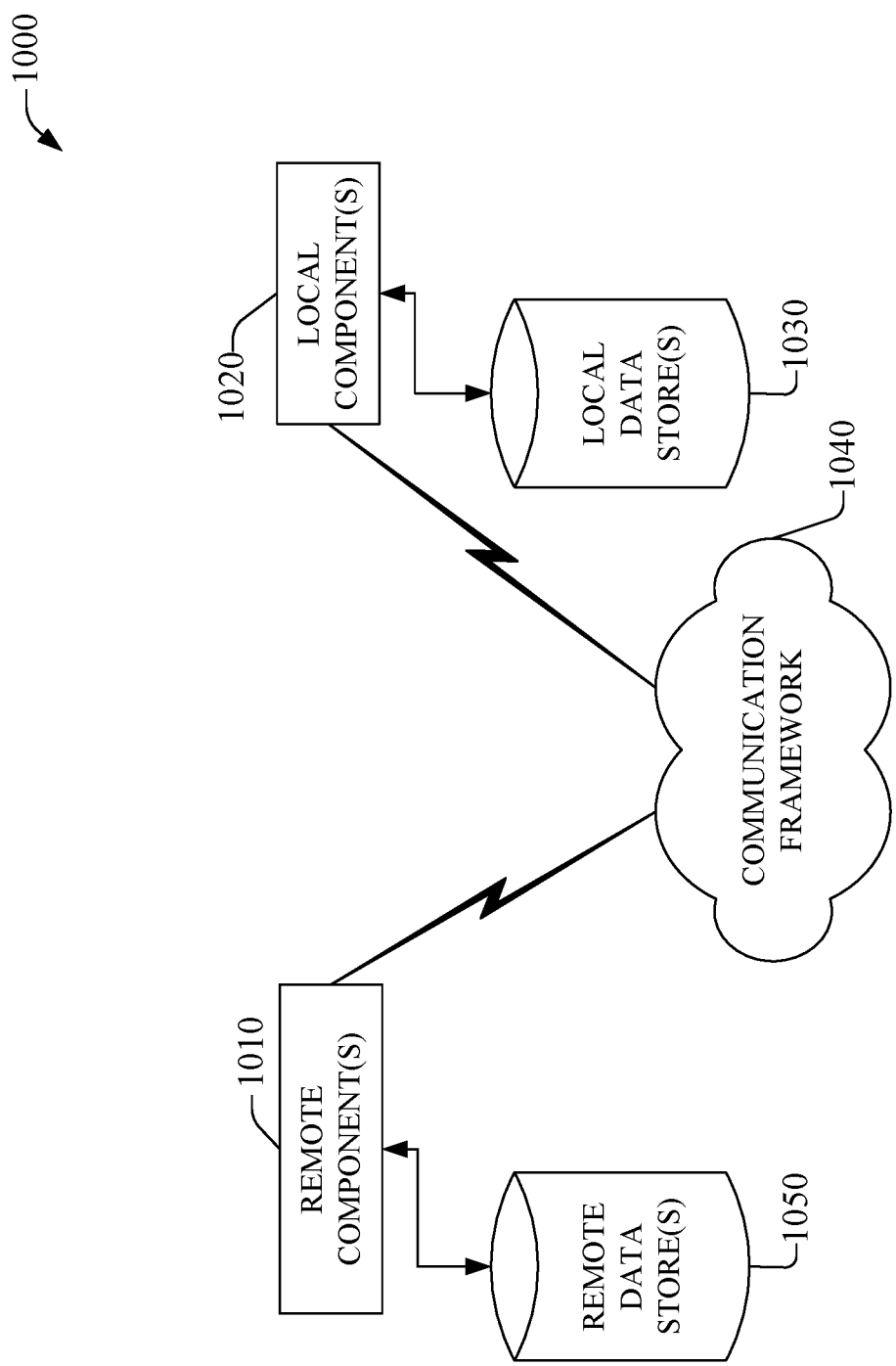
FIG. 10 depicts an example schematic block diagram of a computing environment with which the disclosed subject matter can interact.

FIG. 10 is a schematic block diagram of a computing environment 1000 with which the disclosed subject matter can interact. The system 1000 comprises one or more remote component(s) 1010. The remote component(s) 1010 can be hardware and/or software (e.g., threads, processes, computing devices). In some embodiments, remote component(s) 1010 can comprise servers, personal servers, etc. As an example, remote component(s) 1010 can be a remote server, a controller component, a remotely located compliance component 112, 212, 312, 412, etc., user equipment, laboratory information management system (LIMS) component, etc.

The system 1000 also comprises one or more local component(s) 1020. The local component(s) 1020 can be hardware and/or software (e.g., threads, processes, computing devices). In some embodiments, local component(s) 1020 can comprise, for example, a local compliance component 112, 212, 312, 412, etc., imaging component 130, 230, 330, 430, etc., sample presentation component 120, 220, 320, 420, 520, 620, etc., stage motion component 522, 622, etc.

One possible communication between a remote component(s) 1010 and a local component(s) 1020 can be in the form of a data packet adapted to be transmitted between two or more computer processes. Another possible communication between a remote component(s) 1010 and a local component(s) 1020 can be in the form of circuit-switched data adapted to be transmitted between two or more computer processes in radio time slots. The system 1000 comprises a communication framework 1040 that can be employed to facilitate communications between the remote component(s) 1010 and the local component(s) 1020, and can comprise an air interface, e.g., Uu interface of a UMTS network. Remote component(s) 1010 can be operably connected to one or more remote data store(s) 1050, such as a hard drive, SIM card, device memory, etc., that can be employed to store information on the remote component(s) 1010 side of communication framework 1040. Similarly, local component(s) 1020 can be operably connected to one or more local data store(s) 1030, that can be employed to store information on the local component(s) 1020 side of communication framework 1040.

Figure 11:
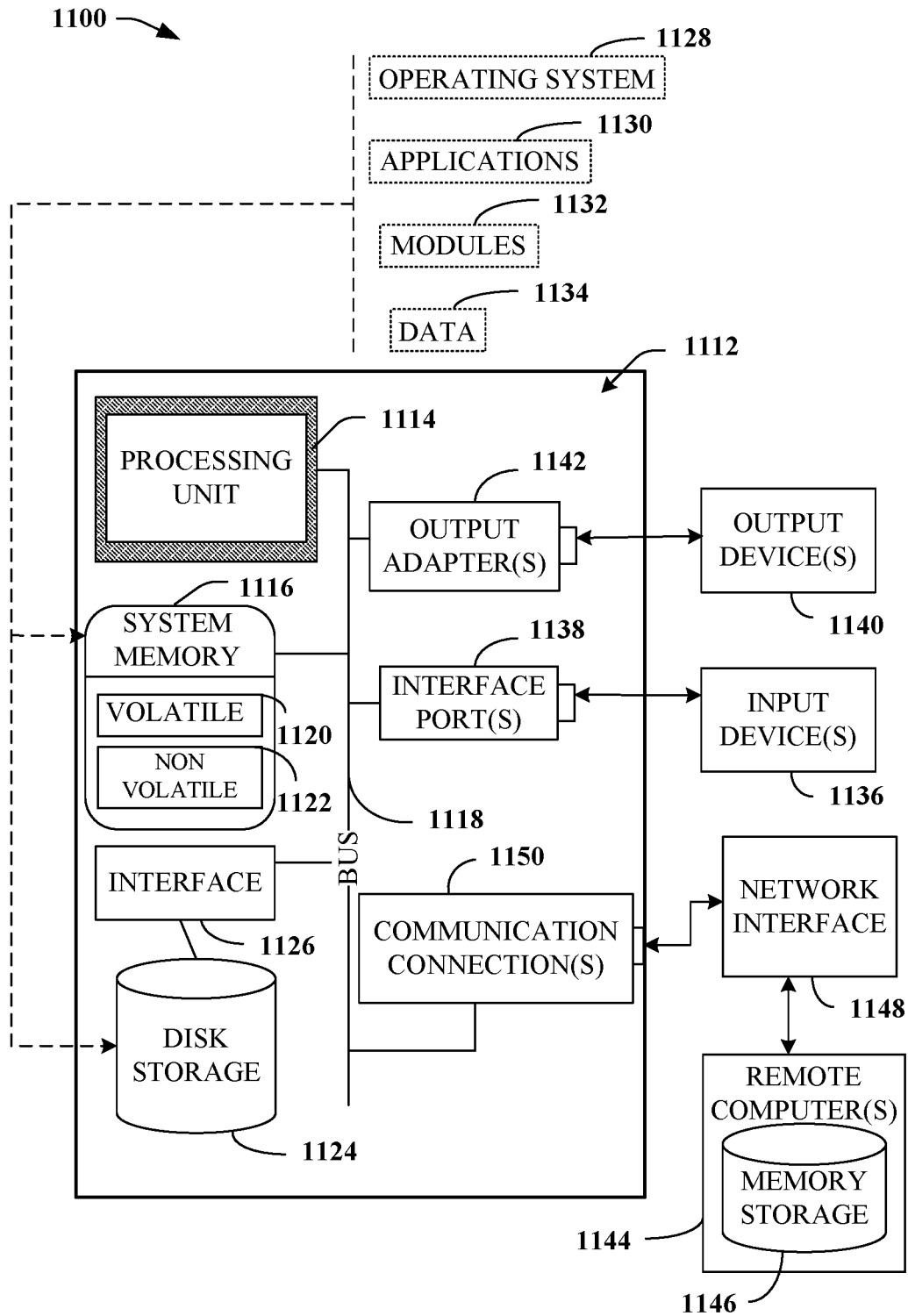
FIG. 11 illustrates an example block diagram of a computing system operable to execute the disclosed systems and methods in accordance with an embodiment.

In order to provide a context for the various aspects of the disclosed subject matter, FIG. 11, and the following discussion, are intended to provide a brief, general description of a suitable environment in which the various aspects of the disclosed subject matter can be implemented. While the subject matter has been described above in the general context of computer-executable instructions of a computer program that runs on a computer and/or computers, those skilled in the art will recognize that the disclosed subject matter also can be implemented in combination with other program modules. Generally, program modules comprise routines, programs, components, data structures, etc. that performs particular tasks and/or implement particular abstract data types.

In the subject specification, terms such as "store," "storage," "data store," data storage," "database," and substantially any other information storage component relevant to operation and functionality of a component, refer to "memory components," or entities embodied in a "memory" or components comprising the memory. It is noted that the memory components described herein can be either volatile memory or nonvolatile memory, or can comprise both volatile and nonvolatile memory, by way of illustration, and not limitation, volatile memory 1120 (see below), nonvolatile memory 1122 (see below), disk storage 1124 (see below), and memory storage 1146 (see below). Further, nonvolatile memory can be included in read only memory, programmable read only memory, electrically programmable read only memory, electrically erasable read only memory, or flash memory. Volatile memory can comprise random access memory, which acts as external cache memory. By way of illustration and not limitation, random access memory is available in many forms such as synchronous random access memory, dynamic random access memory, synchronous dynamic random access memory, double data rate synchronous dynamic random access memory, enhanced synchronous dynamic random access memory, Synchlink dynamic random access memory, and direct Rambus random access memory. Additionally, the disclosed memory components of systems or methods herein are intended to comprise, without being limited to comprising, these and any other suitable types of memory.

Moreover, it is noted that the disclosed subject matter can be practiced with other computer system configurations, comprising single-processor or multiprocessor computer systems, mini-computing devices, mainframe computers, as well as personal computers, hand-held computing devices (e.g., personal digital assistant, phone, watch, tablet computers, netbook computers, . . . ), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

FIG. 11 illustrates a block diagram of a computing system 1100 operable to execute the disclosed systems and methods in accordance with an embodiment. Computer 1112, which can be, for example, comprised in compliance component 112-412, etc., sample presentation component 120-620, etc., stage motion component 522-622, etc., state interaction component 524-624, etc., enclosure 110-410, etc., imaging component 130-430, etc., environmental control component 460, etc., comprises a processing unit 1114, a system memory 1116, and a system bus 1118. System bus 1118 couples system components comprising, but not limited to, system memory 1116 to processing unit 1114. Processing unit 1114 can be any of various available processors. Dual microprocessors and other multiprocessor architectures also can be employed as processing unit 1114.

System bus 1118 can be any of several types of bus structure(s) comprising a memory bus or a memory controller, a peripheral bus or an external bus, and/or a local bus using any variety of available bus architectures comprising, but not limited to, industrial standard architecture, microchannel architecture, extended industrial standard architecture, intelligent drive electronics, video electronics standards association local bus, peripheral component interconnect, card bus, universal serial bus, advanced graphics port, personal computer memory card international association bus, Firewire (Institute of Electrical and Electronics Engineers 1194), and small computer systems interface.

System memory 1116 can comprise volatile memory 1120 and nonvolatile memory 1122. A basic input/output system, containing routines to transfer information between elements within computer 1112, such as during start-up, can be stored in nonvolatile memory 1122. By way of illustration, and not limitation, nonvolatile memory 1122 can comprise read only memory, programmable read only memory, electrically programmable read only memory, electrically erasable read only memory, or flash memory. Volatile memory 1120 comprises read only memory, which acts as external cache memory. By way of illustration and not limitation, read only memory is available in many forms such as synchronous random access memory, dynamic read only memory, synchronous dynamic read only memory, double data rate synchronous dynamic read only memory, enhanced synchronous dynamic read only memory, Synchlink dynamic read only memory, Rambus direct read only memory, direct Rambus dynamic read only memory, and Rambus dynamic read only memory.

Computer 1112 can also comprise removable/non-removable, volatile/non-volatile computer storage media. FIG. 11 illustrates, for example, disk storage 1124. Disk storage 1124 comprises, but is not limited to, devices like a magnetic disk drive, floppy disk drive, tape drive, flash memory card, or memory stick. In addition, disk storage 1124 can comprise storage media separately or in combination with other storage media comprising, but not limited to, an optical disk drive such as a compact disk read only memory device, compact disk recordable drive, compact disk rewritable drive or a digital versatile disk read only memory. To facilitate connection of the disk storage devices 1124 to system bus 1118, a removable or non-removable interface is typically used, such as interface 1126.

Computing devices typically comprise a variety of media, which can comprise computer-readable storage media or communications media, which two terms are used herein differently from one another as follows.

Computer-readable storage media can be any available storage media that can be accessed by the computer and comprises both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can comprise, but are not limited to, read only memory, programmable read only memory, electrically programmable read only memory, electrically erasable read only memory, flash memory or other memory technology, compact disk read only memory, digital versatile disk or other optical disk storage, magnetic cassettes, magnetic tape, magnetic disk storage or other magnetic storage devices, or other tangible media which can be used to store desired information. In this regard, the term "tangible" herein as may be applied to storage, memory or computer-readable media, is to be understood to exclude only propagating intangible signals per se as a modifier and does not relinquish coverage of all standard storage, memory or computer-readable media that are not only propagating intangible signals per se. In an aspect, tangible media can comprise non-transitory media wherein the term "non-transitory" herein as may be applied to storage, memory or computer-readable media, is to be understood to exclude only propagating transitory signals per se as a modifier and does not relinquish coverage of all standard storage, memory or computer-readable media that are not only propagating transitory signals per se. Computer-readable storage media can be accessed by one or more local or remote computing devices, e.g., via access requests, queries or other data retrieval protocols, for a variety of operations with respect to the information stored by the medium. As such, for example, a computer-readable medium can comprise executable instructions stored thereon that, in response to execution, cause a system comprising a processor to perform operations, comprising: enabling emission of optical energy in response to determining concurrent satisfaction of a group of enclosure rules, e.g., via compliance component 112-4112, etc.

Communications media typically embody computer-readable instructions, data structures, program modules or other structured or unstructured data in a data signal such as a modulated data signal, e.g., a carrier wave or other transport mechanism, and comprises any information delivery or transport media. The term "modulated data signal" or signals refers to a signal that has one or more of its characteristics set or changed in such a manner as to encode information in one or more signals. By way of example, and not limitation, communication media comprise wired media, such as a wired network or direct-wired connection, and wireless media such as acoustic, RF, infrared and other wireless media.

It can be noted that FIG. 11 describes software that acts as an intermediary between users and computer resources described in suitable operating environment 1100. Such software can comprise an operating system 1128. Operating system 1128, which can be stored on disk storage 1124, acts to control and allocate resources of computer system 1112. System applications 1130 take advantage of the management of resources by operating system 1128 through program modules 1132 and program data 1134 stored either in system memory 1116 or on disk storage 1124. It is to be noted that the disclosed subject matter can be implemented with various operating systems or combinations of operating systems.

A user can enter commands or information into computer 1112 through input device(s) 1136. In some embodiments, a user interface can allow entry of user preference information, etc., and can be embodied in a touch sensitive display panel, a mouse input GUI, a command line controlled interface, etc., allowing a user to interact with computer 1112. Input devices 1136 comprise, but are not limited to, a pointing device such as a mouse, trackball, stylus, touch pad, keyboard, microphone, joystick, game pad, satellite dish, scanner, TV tuner card, digital camera, digital video camera, web camera, cell phone, smartphone, tablet computer, etc. These and other input devices connect to processing unit 1114 through system bus 1118 by way of interface port(s) 1138. Interface port(s) 1138 comprise, for example, a serial port, a parallel port, a game port, a universal serial bus, an infrared port, a Bluetooth port, an IP port, or a logical port associated with a wireless service, etc. Output device(s) 1140 use some of the same type of ports as input device(s) 1136.

Thus, for example, a universal serial busport can be used to provide input to computer 1112 and to output information from computer 1112 to an output device 1140. Output adapter 1142 is provided to illustrate that there are some output devices 1140 like monitors, speakers, and printers, among other output devices 1140, which use special adapters. Output adapters 1142 comprise, by way of illustration and not limitation, video and sound cards that provide means of connection between output device 1140 and system bus 1118. It should be noted that other devices and/or systems of devices provide both input and output capabilities such as remote computer(s) 1144.

Computer 1112 can operate in a networked environment using logical connections to one or more remote computers, such as remote computer(s) 1144. Remote computer(s) 1144 can be a personal computer, a server, a router, a network PC, cloud storage, a cloud service, code executing in a cloud-computing environment, a workstation, a microprocessor based appliance, a peer device, or other common network node and the like, and typically comprises many or all of the elements described relative to computer 1112.

For purposes of brevity, only a memory storage device 1146 is illustrated with remote computer(s) 1144. Remote computer(s) 1144 is logically connected to computer 1112 through a network interface 1148 and then physically connected by way of communication connection 1150. Network interface 1148 encompasses wire and/or wireless communication networks such as local area networks and wide area networks. Local area network technologies comprise fiber distributed data interface, copper distributed data interface, Ethernet, Token Ring, Radius, Diameter, and the like. Wide area network technologies comprise, but are not limited to, point-to-point links, circuit-switching networks like integrated services digital networks and variations thereon, packet switching networks, and digital subscriber lines. As noted below, wireless technologies may be used in addition to or in place of the foregoing.

Communication connection(s) 1150 refer(s) to hardware/software employed to connect network interface 1148 to bus 1118. While communication connection 1150 is shown for illustrative clarity inside computer 1112, it can also be external to computer 1112. The hardware/software for connection to network interface 1148 can comprise, for example, internal and external technologies such as modems, comprising regular telephone grade modems, cable modems and digital subscriber line modems, integrated services digital network adapters, and Ethernet cards.

The above description of illustrated embodiments of the subject disclosure, comprising what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit, a digital signal processor, a field programmable gate array, a programmable logic controller, a complex programmable logic device, a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

As used in this application, the terms "component," "system," "platform," "layer," "selector," "interface," and the like are intended to refer to a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Further, the term "include" is intended to be employed as an open or inclusive term, rather than a closed or exclusive term. The term "include" can be substituted with the term "comprising" and is to be treated with similar scope, unless otherwise explicitly used otherwise. As an example, "a basket of fruit including an apple" is to be treated with the same breadth of scope as, "a basket of fruit comprising an apple."

Moreover, terms like "user equipment (UE)," "mobile station," "mobile," subscriber station," "subscriber equipment," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "AP," "base station," "Node B," "evolved Node B," "eNodeB," "home Node B," "home access point," and the like, are utilized interchangeably in the subject application, and refer to a wireless network component or appliance that serves and receives data, control, voice, video, sound, gaming, or substantially any data-stream or signaling-stream to and from a set of subscriber stations or provider enabled devices. Data and signaling streams can comprise packetized or frame-based flows.

Furthermore, the terms "user," "subscriber," "customer," "consumer," "prosumer," "agent," and the like are employed interchangeably throughout the subject specification, unless context warrants particular distinction(s) among the terms. It should be appreciated that such terms can refer to human entities or automated components (e.g., supported through artificial intelligence, as through a capacity to make inferences based on complex mathematical formalisms), that can provide simulated vision, sound recognition and so forth.

Aspects, features, or advantages of the subject matter can be exploited in substantially any, or any, wired, broadcast, wireless telecommunication, radio technology or network, or combinations thereof. Non-limiting examples of such technologies or networks comprise broadcast technologies (e.g., sub-Hertz, extremely low frequency, very low frequency, low frequency, medium frequency, high frequency, very high frequency, ultra-high frequency, super-high frequency, terahertz broadcasts, etc.); Ethernet; X.25; powerline-type networking, e.g., Powerline audio video Ethernet, etc.; femtocell technology; Wi-Fi; worldwide interoperability for microwave access; enhanced general packet radio service; third generation partnership project, long term evolution; third generation partnership project universal mobile telecommunications system; third generation partnership project 2, ultra mobile broadband; high speed packet access; high speed downlink packet access; high speed uplink packet access; enhanced data rates for global system for mobile communication evolution radio access network; universal mobile telecommunications system terrestrial radio access network; or long term evolution advanced.

What has been described above includes examples of systems and methods illustrative of the disclosed subject matter. It is, of course, not possible to describe every combination of components or methods herein. One of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A device, comprising:
 a probe to facilitate performing optical spectroscopy of a sample;
 a processor; and
 a memory that stores executable instructions that, when executed by the processor, facilitate performance of operations, comprising:
 receiving an indication that the probe is in contact with the sample;
 determining that a group of rules comprising a first rule is concurrently satisfied, wherein the first rule relates to a contact condition of the sample based on the indication that the probe is in contact with the sample; and
 in response to the determining that the group of rules is concurrently satisfied, enabling emission of first optical energy to interrogate the sample via the probe.

2. The device of claim 1, wherein the operations further comprise, in response to the determining that the group of rules is not concurrently satisfied, restricting emission of the first optical energy.

3. The device of claim 1, wherein the group of rules further comprises a second rule related to determining than an enclosure of the device is in a first position that facilitates operation of the device to perform the optical spectroscopy of the sample.

4. The device of claim 1, wherein the group of rules further comprises a second rule related to determining that an ambient light level within an enclosure of the device has transitioned a threshold level.

5. The device of claim 4, wherein the ambient light level corresponds to a decay of fluorescent optical energy resulting from artificial illumination of a florescent compound.

6. The device of claim 1, further comprising an imaging device configured to provide access to images of an interior of an enclosure of the device, wherein the probe contacts the sample within the enclosure.

7. The device of claim 1, further comprising an environmental control device configured to control an environmental condition within an enclosure of the device, wherein the probe contacts the sample within the enclosure.

8. The device of claim 7, wherein the environmental condition is temperature, pressure, humidity, or atmospheric composition.

9. The device of claim 8, wherein the atmospheric composition results in an inert gaseous environment.

10. The device of claim 1, further comprising a viewport enabling direct visualization, through an enclosure of the device, of the probe in contact with the sample within the enclosure.

11. The device of claim 10, wherein the viewport comprises a window material that attenuates the transmission of optical energy within a spectral region.

12. The device of claim 11, wherein the spectral region corresponds to a frequency of the first optical energy employed to interrogate the sample.

13. The device of claim 1, further comprising a store of exchangeable probe tips, and wherein the probe can contact the sample via an exchangeable probe tip selected from the store of exchangeable probe tips.

14. The device of claim 1, further comprising a cleaning device enabling cleaning of the probe.

15. The device of claim 1, wherein the optical spectroscopy is Raman spectroscopy.

16. A system, comprising:
   an enclosed optical analysis device, comprising:
      a probe portion that channels optical energy as part of interrogating a sample;
      a sample holder that positions the sample for interrogation via the probe portion; and
      a compliance component that enables the release of the optical energy in response to determining concurrent compliance of a group of compliance rules, wherein the group of compliance rules comprises a first compliance rule related to contact between the probe portion and the sample; and
   a user equipment communicatively coupled to the enclosed optical analysis device to:
      enable adapting the group of compliance rules; and
      enable adapting the position of the sample for interrogation via the probe portion.

17. The system of claim 16, wherein the enclosed optical analysis device performs Raman spectroscopy.

18. The system of claim 16, wherein the adapting the group of compliance rules comprises modifying a compliance rule of the group of compliance rules, adding a compliance rule to the group of compliance rules, or removing a compliance rule from the group of compliance rules.

19. A method, comprising:
   enabling, by a system comprising a processor, release of optical energy in response to determining concurrent compliance of compliance rules comprising a first compliance rule, wherein the first compliance rule is determined to be satisfied based on contact between a spherical optical element of a Raman spectroscopy probe and a sample within an enclosure of a Raman spectrometer; and
   restricting, by the system, release of the optical energy in response to determining a lack of concurrent compliance of the compliance rules.

20. The method of claim 19, wherein the compliance rules further comprise:
   a second compliance rule relating to a level of ambient light within the enclosure;
   a third compliance rule relating to the enclosure being closed;
   a fourth compliance rule relating to a state of a viewport through a wall of the enclosure;
   a fifth rule relating to an environmental condition within the enclosure; or
   a sixth rule relating to a level of light transmission via the spherical optical element of the Raman spectroscopy probe.

* * * * *